US008155487B2

(12) United States Patent
Irawan et al.

(10) Patent No.: US 8,155,487 B2
(45) Date of Patent: Apr. 10, 2012

(54) SENSOR ELEMENT

(75) Inventors: Rudi Irawan, Singapore (SG); Ieng Kin Lao, Taipa (MO)

(73) Assignee: Nitto Denko Corporation, Ibaraki Osaka (JP)

( * ) Notice: Subject to any disclaimer, the term of this patent is extended or adjusted under 35 U.S.C. 154(b) by 360 days.

(21) Appl. No.: 12/534,245

(22) Filed: Aug. 3, 2009

(65) Prior Publication Data
US 2011/0026871 A1 Feb. 3, 2011

(51) Int. Cl.
*G02B 6/00* (2006.01)
(52) U.S. Cl. ........ 385/12; 385/43; 435/288.7; 356/73.1; 356/432
(58) Field of Classification Search ............ 385/12, 385/13, 43; 436/167; 435/288.7; 356/73.1, 356/432, 477
See application file for complete search history.

(56) References Cited

U.S. PATENT DOCUMENTS

| | | | |
|---|---|---|---|
| 5,170,056 A * | 12/1992 | Berard et al. | 250/341.2 |
| 5,173,747 A * | 12/1992 | Boiarski et al. | 356/481 |
| 5,663,790 A * | 9/1997 | Ekstrom et al. | 356/128 |
| 6,429,023 B1 | 8/2002 | Gharavi | |
| 6,605,804 B1 | 8/2003 | Muller-Fiedler et al. | |
| 7,019,847 B1 * | 3/2006 | Bearman et al. | 356/517 |
| 7,497,992 B2 | 3/2009 | Cunningham et al. | |
| 7,498,145 B2 | 3/2009 | Uchiyama et al. | |
| 7,801,394 B2 * | 9/2010 | Tang et al. | 385/12 |
| 7,820,983 B2 * | 10/2010 | Lundquist et al. | 250/458.1 |
| 2007/0099292 A1 | 5/2007 | Miller et al. | |
| 2008/0231857 A1 * | 9/2008 | Depeursinge et al. | 356/437 |

FOREIGN PATENT DOCUMENTS

| | | | |
|---|---|---|---|
| GB | 2307741 A | * | 6/1997 |
| WO | 2008110927 A2 | | 9/2008 |

* cited by examiner

*Primary Examiner* — Daniel Petkovsek

(57) ABSTRACT

In an embodiment, a sensor element is provided. The sensor element may include a light input configured to receive input light, a sample chamber configured to accommodate a sample, and at least one polymer waveguide optically coupling the light input with the sample chamber, the at least one polymer waveguide including a first contact portion and a second contact portion, wherein at least a portion of the second contact portion may be arranged in the sample chamber. The second contact portion may include a different structure than the first contact portion so that a change of the light intensity of the input light passing through the second contact portion may be caused due to an interaction between the input light passing through the second contact portion and the sample, wherein the change of the light intensity of the input light passing through the second contact portion may be different from the change of the light intensity of the input light passing through the first contact portion.

18 Claims, 23 Drawing Sheets

SENSOR ELEMENT

TECHNICAL FIELD

Embodiments relate to a sensor element.

BACKGROUND

Measuring or detecting molecules or analytes in samples is a rapidly growing demand in environmental, medical, agricultural, chemical and industrial sectors. In the environmental sector, such sensors or detectors may be employed to measure certain molecule contents inside city water or reservoirs. For the medical sector, such devices may be employed for measuring or detecting biomolecules as disease markers in situ and/or continuously.

It is common in the medical field to measure the concentration of molecules in fluids obtained from patients. The demand for new tests of blood or urine chemistry has increased rapidly, with resultant growth of centralized testing laboratories. The current performance of quantitative diagnostic or screening tools may be largely restricted to centralized laboratories because of the need for long assay times, and relatively bulky, complex and expensive analytical equipment, as well as highly trained personnel. If a wider range of the diagnostic and health monitoring tools may be run simpler, more inexpensively and at the point of care or in the home healthcare, the health of millions patients may be improved annually, particularly for old people who often need regular health monitoring or check up but have difficulties to visit the healthcare facilities.

Therefore, there is a need for a simple, compact, smart, robust and inexpensive sensor element which can provide high quality results.

SUMMARY

In various embodiments, a sensor element is provided. The sensor element may include a light input configured to receive input light, a sample chamber configured to accommodate a sample and at least one polymer waveguide optically coupling the light input with the sample chamber, the at least one polymer waveguide may include a first contact portion and a second contact portion, wherein at least a portion of the second contact portion may be arranged in the sample chamber. The second contact portion may include a different structure than the first contact portion so that a change of the light intensity of the input light passing through the second contact portion may be caused due to an interaction between the input light passing through the second contact portion and the sample and wherein the change of the light intensity of the input light passing through the second contact portion may be different from the change of the light intensity of the input light passing through the first contact portion.

BRIEF DESCRIPTION OF THE DRAWINGS

In the drawings, like reference characters generally refer to the same parts throughout the different views. The drawings are not necessarily to scale, emphasis instead generally being placed upon illustrating the principles of various embodiments. In the following description, various embodiments of the invention are described with reference to the following drawings, in which.

DESCRIPTION

Figure 1:
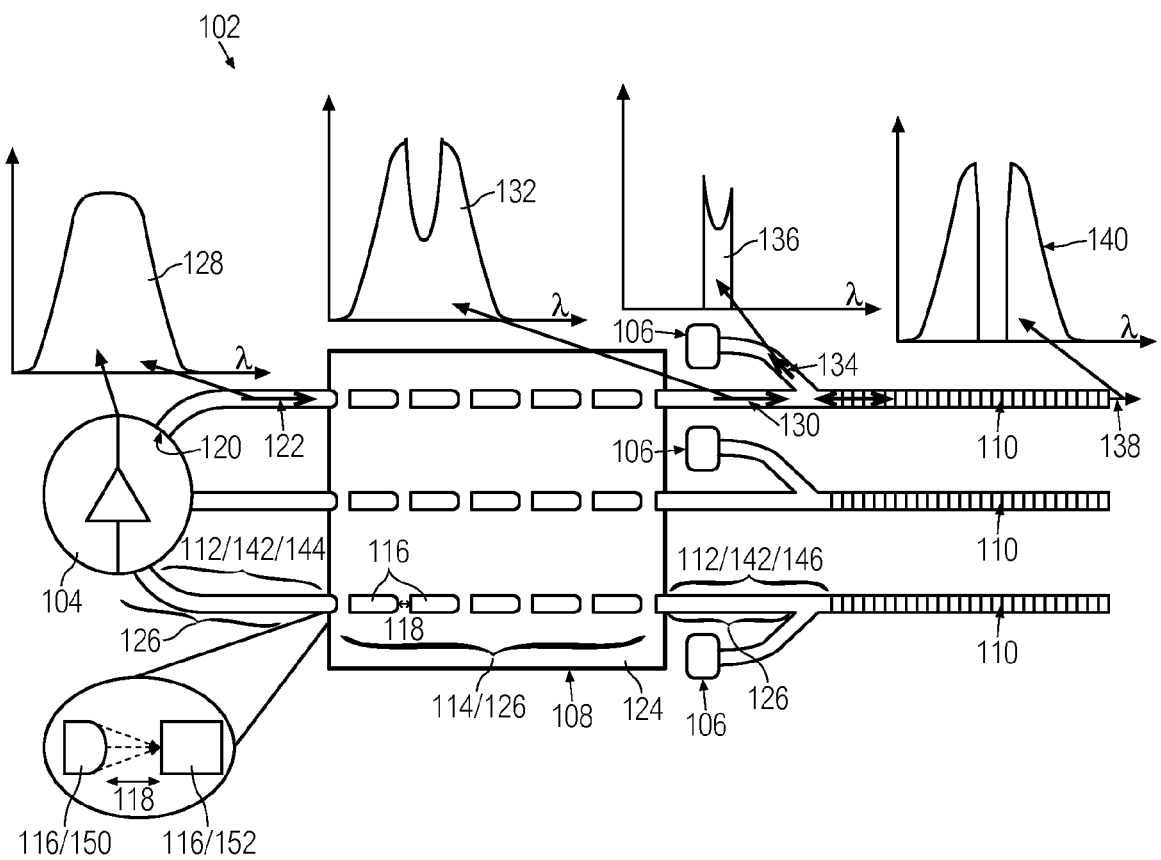
FIG. 1 shows a top view of a sensor element with a light source and three optical detectors respectively positioned on two opposite sides of a sample chamber, three Bragg grating filters and a second contact portion including at least two shaped portions, each shaped portion separated by a gap according to an embodiment.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

The word "exemplary" is used herein to mean "serving as an example, instance, or illustration". Any embodiment or design described herein as "exemplary" is not necessarily to be construed as preferred or advantageous over other embodiments or designs.

In various embodiments, a sensor element may be provided, which may reduce the cost and size of detecting or measuring target molecules within a sample while maintaining or enhancing the sensitivity.

An embodiment provides a sensor element. The sensor element may include a light input configured to receive input light, a sample chamber configured to accommodate a sample, and at least one polymer waveguide optically coupling the light input with the sample chamber, the at least one polymer waveguide including a first contact portion and a second contact portion, wherein at least a portion of the second contact portion may be arranged in the sample chamber. The second contact portion may include a different structure than the first contact portion so that a change of the light intensity of the input light passing through the second contact portion may be caused due to an interaction between the input light passing through the second contact portion and the sample, wherein the change of the light intensity of the input light passing through the second contact portion may be different from the change of the light intensity of the input light passing through the first contact portion.

In an embodiment, at least a portion of the at least one polymer waveguide may be positioned in the sample chamber. As an example, the first contact portion and the second contact portion may be positioned substantially within the sample chamber, only a portion of the first contact portion and the second contact portion may be positioned in the sample chamber or only the second contact portion may be positioned in the sample chamber.

In an embodiment, there may be more than one polymer waveguide. As an example, there may be three polymer waveguides. In alternative embodiments, more than three waveguides, e.g. an arbitrary number of waveguides, may be provided. The first and the second polymer waveguides may be spaced at a first distance along the length of the respective first and second polymer waveguides away from each other. Further, the second and the third polymer waveguides may be spaced at a second distance along the length of the respective second and third polymer waveguides away from each other. The first distance and the second distance may be substantially the same or different from each other. The first distance may be in the range of about in order of 5 μm to 5 cm, typically about 2 mm and the second distance may be in the range of about in order of 5 μm to 5 cm, typically about 2 mm. The first distance may be the same or different from the second distance.

In an embodiment, the second contact portion may be a single portion or may include two or more second partial contact portions. The two second partial contact portions may be the same or different from each other. The number of the second partial contact portions may vary depending on design and user requirements.

In an embodiment, at least a portion of the first contact portion may be positioned outside of the sample chamber. The portion of the first contact portion positioned outside of the sample chamber may include two first partial contact portions, for example a portion optically coupling the sample chamber to a light source and/or a portion optically coupling the sample chamber to at least one filter or to at least one optical detector. The portion of the first contact portion positioned outside of the sample chamber may include three first partial contact portions, for example a portion optically coupling the sample chamber to a light source and/or a portion optically coupling the sample chamber to at least one filter and/or a portion optically coupling the two second partial contact portions. The number of first partial contact portion may vary depending on design and user requirements. Each first partial contact portion may be the same or different from each other depending on design and user requirements.

In an embodiment, each of the second contact portion may be positioned parallel to each other within the sample chamber. By way of example, the axis of each of the second contact portion may be positioned parallel to each other within the sample chamber. Each of the second contact portion may be spaced apart by an equal or a different distance along the length of the second contact portion from each other. The distance between each second contact portion may be in the range of about in order of 5 μm to about 5 cm, typically about 2 mm.

In an embodiment, the sensor element may further include at least one optical detector positioned in optical communication with the at least one polymer waveguide for detecting a resultant light after the input light travels along the at least one polymer waveguide and through the sample chamber. The at least one optical detector may include one or more of a group consisting of a photodiode, a photomultiplier, a charged-coupled device (CCD) detector, a light dependent resistor (LDR), a phototransistor and a photocell for example. The at least one optical detector may be positioned directly in contact with the sample chamber or at any suitable distance away from the sample chamber.

In an embodiment, the sensor element may further include at least one optical filter configured to output a pre-determined wavelength of the resultant light, the at least one optical filter being positioned in the optical path between the at least one polymer waveguide and the at least one optical detector. The at least one optical filter may include one or more of a group consisting of a Bragg grating filter or a Fabry-perot filter, absorptive filter, dichroic filter and interference filter for example. The transmission spectrum of the Bragg grating filter may behave like a notch filter, while the reflection spectrum may behave like a band pass filter which may have the centre wavelength as the centre wavelength of absorption wavelength of a target analyte in the sample housed in the sample chamber. The Fabry-Perot filter may behave like a band-pass filter which may have a centre of transmission the same as the centre of absorption of a target analyte in the sample housed in the sample chamber. The at least one optical filter may or may not be necessarily present in the sensor element.

In an embodiment, a detected light spectrum may be the spectrum as seen by the at least one optical detector. In a Bragg grating filter, the reflection spectrum may be considered as the detected light spectrum but in a Fabry-Perot filter, the transmission spectrum may be considered as the detected light spectrum.

In an embodiment, the at least one optical filter may be optional if the input source is of the desired wavelength.

In an embodiment, the at least one optical filter may be also be coated directly on the light source, on the at least optical detector or developed within the at least one polymer waveguide.

In an embodiment, the first contact portion may include a continuous portion with a constant diameter. The diameter or height of the first contact portion may be in the range of about 5 μm to 2 mm, typically about 250 μm. The length of the first contact portion may be in the range of about 1 mm to 5 cm, typically about 1.5 cm. The cross-section of the first contact portion may be circular, rectangle, square, triangle, or any other suitable shapes. The dimensions and shape of the first contact portion may vary depending on user and design requirements.

In an embodiment, the second contact portion may be configured so as to allow an increased interaction between the input light and the sample as compared to the first contact portion.

In an embodiment, the second contact portion may include at least two shaped portions positioned along a common axis, each shaped portion separated by a gap. There may be more than two shaped portions, for example in the range of about 2 to 100, typically 20. There may also be more than one gap, for example in the range of about 1 to 100, typically about 20. The number of gaps along the second contact portion may depend on the light source and dimension of the at least one polymer waveguide. Each gap may be spaced at a regular or a varying interval along the length of the second contact portion. The distance of each gap may be in the range of about 5 μm to about 1 cm, typically about 2.5 mm. The distance of each gap may depend on the refractive index of the sample housed within the sample chamber and on the width of the at least one polymer waveguide. The overall path length or the sum of all the gaps along the second contact portion may also be termed the interaction length.

Each shaped portion may include a rounded portion and an elongated portion. The rounded portion of one shaped portion may be configured for directly the input light onto the elongated portion of another shaped portion. The shaped portion may also be of any other suitable shapes depending on user and design requirements. Each shaped portion may be of the same or different from the other shaped portion. For example, the shape or dimension of each shaped portion may be the same or different from the other shaped portion. Further, one shaped portion may be arranged relative to another shaped portion such that there may be an overlapping portion or no overlapping portion, e.g. overlapping in the direction of the light propagation throught the at least one polymer waveguide.

For the second contact portion with at least two shaped portions and each shaped portion separated by a gap, light-sample interaction may occur in the polymer waveguide. The input light interacts with the sample housed in the sample chamber directly. Light-sample interactions may occur in the plurality of gaps in the second contact portion of the polymer waveguide. Input light exiting one shaped portion at an input side of one gap may be self-focused by the shaped portion onto another shaped portion at an output side of the gap. The multiple direct interaction between the input light and the sample in the sample chamber may enhance the sensitivity of the sensor element.

In an embodiment, the second contact portion may include a continuous portion with at least one hole, each of the at least one hole being spaced from another at a regular interval or varying interval along the length of the continuous portion. The distance between each of the at least one hole may be in the range of about 100 μm to about 10 cm, typically about 2 mm. There may be in the range from about 1 to about 50 holes, e.g. in the range from about 1 to 30 holes, e.g. in the range from about 1 to 20 holes. Each of the holes may be circular, rectangle, triangle in shape or of any suitable shape. The diameter of each of the holes may be in the range of about 5 μm to about 1 mm, e.g. about 250 μm. Varying the number of holes along the continuous portion may enhance the sensitivity of the sensor element. The holes serve to enhance the light-sample interactions. The holes may be positioned along a common axis along the length of the continuous portion or it may be randomly distributed along the length of the continuous portion. The holes may be arranged in any suitable manner and there may be any suitable number of holes depending on design and user requirement.

For the second contact portion with the continuous portion with at least one hole, light-sample interaction may occur in the polymer waveguide. The input light interacts with the sample housed in the sample chamber directly. Light-sample interactions may occur in the plurality of holes in the second contact portion of the polymer waveguide. Input light exiting the second contact portion at the holes may be self-coupled back into the waveguides. The multiple direct interactions between the input light and the sample in the sample chamber may enhance the sensitivity of the sensor element.

In an embodiment, the second contact portion may include a continuous portion with a varying diameter along the length of the second contact portion. The diameter may vary according to a predefined pattern along the length of the second contact portion or may just decrease and/or increase along the length of the second contact portion. The diameter variation may be in the range of about 5 µm to about 1 mm, e.g. about 300 µm.

In an embodiment, the second contact portion may include a first tapered portion and a second tapered portion. The first tapered portion and the second tapered portion may be the same or different from each other. Each of the first tapered portion and the second tapered portion may include a conical portion with a tapered end and an enlarged end. The diameter or dimension of the enlarged end may be larger than the tapered end. Each of the tapered end of the first tapered portion and the second tapered portion may include a diameter in the range of about 3 µm to about 1 mm, typically about 200 µm. Each of the enlarged end of the first tapered portion and the second tapered portion may include a diameter in the range of about 5 µm to about 2 mm, typically about 500 µm.

In an embodiment, the first tapered portion may be in optical communication with the second tapered portion. As an example, the tapered end of the first tapered portion and the tapered end of the second tapered portion may be in direct contact with each other so as to form a narrower path or a conical optical sensing area for the passage of input light as compared to the enlarged end of the respective first and second tapered portions.

In an embodiment, the second contact portion may further include an intermediate tapered portion positioned between the first tapered portion and the second tapered portion, the intermediate tapered portion in optical communication with the first tapered portion and the second tapered portion. By way of example, each end of the intermediate tapered portion may be in optical communication with the tapered end of the respective first tapered portion and the second tapered portion. The intermediate tapered portion may be an elongated portion with a length in the range of about 1 µm to about 10 cm, e.g. about 1 mm. The intermediate tapered portion may include a constant or varying diameter along the length of the intermediate tapered portion. The diameter of the intermediate tapered portion may be in the range of about 3 µm to about 1 mm, e.g. about 200 µm.

In an embodiment, the input light may travel along the at least one polymer waveguide. Even though the light energies may be totally reflected within the at least one polymer waveguide, the electromagnetic fields may still penetrate into the second medium or outside of the at least one polymer waveguide. These electromagnetic fields or standing waves, may decay exponentially away from the boundary into the low refractive index medium and propagate parallel to the boundary of the surface. This wave is called evanescent wave. Hence, the evanescent wave may interact with the medium surrounding the polymer waveguide, which may be a sample to be measured (measurand), and the interaction between the evanescent wave and the measurand may cause the absorption of input light. For the sensing purpose, one parameter may be the penetration depth of the exponentially decaying evanescent wave or field which may be enhanced by suppressing the input light or light wave propagating inside the at least one polymer waveguide. The deeper the penetration depth of evanescent field may be, the stronger the interaction of light with the surrounding medium which may affect the light propagating along the at least one polymer waveguide.

In an embodiment, the light-sample interaction may be enhanced by shaping the at least one polymer waveguide conically. Besides being determined by the penetration depth of the evanescent wave into the surrounding medium (or sample), the light absorption may also be dictated by the interaction length between the light and the surrounding medium. According to Beer-Lambert law, light absorption due to interaction length is governed by this equation $$I = I_0 e^{-\alpha x}, \quad (1)$$

where
   I is the measured intensity of transmitted light through a layer of material with length x (in the following also referred to as path length) related to the incident intensity $I_0$; and
   α denotes the attenuation coefficient or linear attenuation coefficient.

Therefore, the larger the length (path length) x may be, the better the sensitivity may be. In a relatively big device or equipment, a large length (path length) x can be achieved by focusing light into a sample cuvette using a set of optical lenses. A large length (path length) x may also be achieved in evanescent wave interactions using conically shaped polymer waveguide because light may still be consistently contained inside the at least one polymer waveguide, such as in the conical waveguide sensing area.

For the second contact portion with the first tapered portion and the second tapered portion and/or the intermediate tapered portion, light-sample interaction occur outside of the polymer waveguide. The input light interacts with the sample housed in the sample chamber via the evanescent field. The light-sample interactions via the evanescent field may be enhanced by the conical shaped sensing area of the polymer waveguide. The intensity of the evanescent field depends on the refractive index of the sample housed within the sample chamber and the size of the polymer waveguide. The smaller the dimension, the higher the intensity of the evanescent field, thereby the higher the light-sample interaction. Input light exiting the at least one polymer waveguide via the evanescent field may be self-coupled into the at least one polymer waveguide. The combination of the enhanced evanescent field and the length of the conical shaped sensing area may enhance the sensitivity of the sensor element.

In an embodiment, the second contact portion may include a spiral portion or a U-shaped portion. The second contact portion may include any suitable configurations as long as the configuration allows an increased interaction between the input light and the sample, whether directly or indirectly.

In an embodiment, the sensor element further includes a light source configured to provide the input light to the light input. The light source adopted may provide the input light which may cover the absorption range of the target analyte or molecule of interest in the sample.

In an embodiment, all analytes in body fluid may absorb light intrinsically at certain wavelengths. However, the intrinsic absorption of the body fluid may not be convenient to be detected. Many of the body fluid or material may absorb light at an ultraviolet range or region, and with low intensity and less specificity. One way to increase the intensity and specificity may be such that a chemical reagent or colouring reagent may be commonly added into a body fluid measurand. The specific chemical reagent may react with a specific analyte in the body fluid, thereby changing the colour of the body fluid. The colour of fluid may cause light to be absorbed at a certain wavelength range. Hence, the analyte may be measured using a colorimetric absorption technique. Usually, the level of the colour may be proportional to the concentration of the target analyte in the body fluid.

Therefore, colouring reagents for a particular wavelength may be introduced into the sample to further enhance the sensitivity of the sensor element and to specify the absorption wavelength range. The input light may interact with the sample, such as urine, and a specific colouring reagent, which may produce a specific colour after the sample react with the specific colouring reagent.

In an embodiment, the light source may include one or more of a group consisting of a laser, a white light, a fluorescent light, a laser diode, a light emitting diode (LED), an organic light emiting diode (OLED), a gas discharge light source, an incandescent lamp and an electroluminescent lamp for example. The light source may include a single wavelength or multiple wavelengths.

In an embodiment, the sample chamber may include circular shape, a rectangle shape, a square shape, a triangle shape or any suitable shapes. The dimensions of the sample chamber may include a height of about 100 µm to about 5 cm, e.g. about 2 mm, a breadth of about 1 mm to about 10 cm, e.g. about 1 cm and a length of about 1 cm to about 20 cm, e.g. about 5 cm. The sample chamber may be made of any suitable material, for example polymer.

In an embodiment, the light source and the at least one optical detector may be positioned on two opposite or different sides of the sample chamber. By way of example, the light source may be positioned on one side of the sample chamber and the at least one optical detector may be positioned on an opposite side of the sample chamber. Of the light source may be positioned on one side of the sample chamber and the at least one optical detector may be positioned on an adjacent side of the sample chamber.

In an embodiment, the light source and the at least one optical detector may be positioned on a same side of the sample chamber.

In an embodiment, the light source and the at least one optical detector may be arranged in a first device. The dimensions of the first device may include a height of about 0.5 cm to about 10 cm, typically about 5 cm, a breadth of about 0.5 cm to about 20 cm, e.g. about 10 cm and a length of about 2 cm to about 30 cm, e.g. about 10 cm. The first device may include other electronics components if necessary. The first device may be made of polymer material, metals, and glasses for example.

In an embodiment, the sample chamber and the at least one polymer waveguide may be arranged in a second device. The dimensions of the second device may include a height of about 100 µm to about 5 cm, e.g. about 1 cm, a breadth of about 1 mm to about 10 cm, e.g. about 1 cm and a length of about 1 cm to about 25 cm, e.g. about 6.5 cm. The second device may include polymer material for example.

In an embodiment, the dimensions of the first device may be comparable to or different from the dimensions of the second device. The material of the first device may be the same or different from the material of the second device. The first device and the second device may also be a single unit.

In an embodiment, the second device may be detachably coupled from the first device through the concept of plug-and-play.

In an embodiment, the sensor element may further include a further sample chamber configured to accommodate a further sample. The further sample chamber may be the same or different from the sample chamber. There may be more than one further sample chambers. The number of sample chamber or further sample chamber may depend on user and design requirements. The sample chamber and/or the further sample chamber may be disposable and may be replaced whenever necessary. The sample chamber and the further sample chamber may be termed the biosensor card and further biosensor card respectively.

In an embodiment, the further sample may be the same or different from the sample. The sample may include macromolecular biomolecules, molecules of interest or target analyte. The sample may include urine, blood, DNA molecules, proteins, saliva, stool, sweat for example.

In an embodiment, the sensor element may further include a further polymer waveguide optically coupling the further sample chamber with the light input. There may be more than one further polymer waveguide. The number of the at least one polymer waveguide or the further polymer waveguide may depend on user and design requirements.

In an embodiment, the at least a portion of the further polymer waveguide may be arranged in the further sample chamber.

In an embodiment, the further polymer waveguide may be the same or different from the at least one polymer waveguide. By way of example, the shape or dimension of the further polymer waveguide may be the same or different from the at least one polymer waveguide.

In an embodiment, the sensor element may further include a further optical detector, the further optical detector may be positioned in optical communication with the further polymer waveguide for detecting a further resultant light after the input light travels along the further polymer waveguide and through the further sample chamber. The further resultant light may be substantially similar or different from the resultant light. This may depend on the sample housed within the sample chamber and the dimensions of the at least one polymer waveguide and further polymer waveguide for example.

In an embodiment, the further optical detector may be the same or different from the at least one optical detector. The number of at least one optical detector and the further optical detector may vary depending on user and design requirements.

In an embodiment, the sensor element may further include a display unit. There may be more than one display units, depending on user and design requirements.

In an embodiment, the light source, the at least one optical detector, the further optical detector and the display unit may be arranged or housed in the first device.

In an embodiment, the sample chamber, the at least one polymer waveguide, the further sample chamber and the further polymer waveguide may be arranged or housed in the second device.

In an embodiment, the sample chamber and the at least polymer waveguide may be arranged or housed in one device and the further sample chamber and the further polymer waveguide may be arranged or housed in another device.

In an embodiment, the light source, the at least one polymer waveguide, the sample chamber, the at least one optical detector may be in a single device. Further, the at least one filter may be in the same single device. Even further, the at least one further polymer waveguide, the further sample chamber and the further optical detector may be in the same single device. All the respective components within the sensor element may be in a single device or in separate devices depending on user and design requirements.

In an embodiment, a sensor element or optical sensor may be disclosed. The sensor element may be configured for detecting or measuring target analyte or target molecules using the polymer optical waveguides. By way of example, the sensor element may be configured for measuring the concentration of the target analyte or target molecules within the sample.

In an embodiment, light absorption at a particular wavelength may be based on direct interaction between light and target molecules using microstructures of multiple gaps of the at least one polymer optical waveguides. The microstructures of multiple gaps may function to enable the input light to interact directly with the target molecules and to focus the light into the next portions of the at least one polymer waveguide.

In an embodiment, light absorption at a particular wavelength may be based on a direct interaction between light and target molecules using microstructures of multiple microholes within the polymer optical waveguides. The microstructures of multiple microholes may function to enable the input light to interact directly with the target molecules, but still containing the input light within the at least one polymer waveguide.

In an embodiment, light absorption at a particular wavelength may be based on interaction between the evanescent wave of light propagating through the at the least one polymer waveguide and target molecules using microstructures of conically shaped polymer optical waveguides. The conically shaped microstructures may function to enhance the evanescent wave light interaction with the target molecules, but still containing the input light within the at least one polymer waveguide.

In an embodiment, the at least one polymer waveguide may further include an intermediate contact portion, the intermediate contact portion may be positioned between the first contact portion and the second contact portion.

An embodiment provides a sensor arrangement. The sensor arrangement may include a sensor element including a light input configured to receive input light; a sample chamber configured to accommodate a sample; at least one polymer waveguide optically coupling the light input with the sample chamber, the at least one polymer waveguide including a first contact portion and a second contact portion, wherein at least a portion of the second contact portion is arranged in the sample chamber; at least one optical detector positioned in optical communication with the at least one polymer waveguide for detecting a resultant light after the input light travels along the at least one polymer waveguide and through the sample chamber; and a light source configured to provide the input light to the light input. The sensor arrangement may further include a first device including the light source and the at least one optical detector; and a second device including the sample chamber and the at least one polymer waveguide. The second contact portion may include a different structure than the first contact portion so that a change of the light intensity of the input light passing through the second contact portion may be caused due to an interaction between the input light passing through the second contact portion and the sample, wherein the change of the light intensity of the input light passing through the second contact portion may be different from the change of the light intensity of the input light passing through the first contact portion.

In an embodiment, the second device may be detachably coupled with the first device.

In an embodiment, the first device may include a slot or socket configured for receiving a portion of the second device.

In an embodiment, the sensor arrangement may further include a guiding element configured to allow the second device to be mechanically aligned to the first device.

FIG. 1 shows a top view of a sensor element 102 with a light source 104 and three optical detectors 106 respectively positioned on two opposite sides of a sample chamber 108, three Bragg grating filters 110 and a second contact portion 114 including at least two shaped portions 116, each shaped portion 116 separated by a gap 118 according to an embodiment. Thus, illustratively, in various embodiments, a plurality of gaps 118 may be provided in case of a multiplicity of shaped portions 116 being separated from each other.

The sensor element 102 may include a light input 120 configured to receive input light 122, a sample chamber 108 configured to accommodate a sample 124 and three polymer waveguides 126 optically coupling the light input 120 with the sample chamber 108, each of the three polymer waveguides 126 including a first contact portion 112 and a second contact portion 114, wherein at least a portion of the second contact portion 114 may be arranged in the sample chamber 108. The second contact portion 114 may include a different structure than the first contact portion 112 so that a change of the light intensity of the input light 122 passing through the second contact portion 114 may be caused due to an interaction between the input light 122 passing through the second contact portion 114 and the sample 124 and wherein the change of the light intensity of the input light 122 passing through the second contact portion 114 may be different from the change of the light intensity of the input light 122 passing through the first contact portion 112.

The sensor element 102 further includes a light source 104 configured to provide the input light 122 to the light input 120. The light source 104 may include a laser, a fluorescent light, a laser diode, a light emitting diode (LED), an organic LED (OLED), a gas discharge light source, an incendescent lamp, an electroluminescent lamp for example.

The sensor element 102 may further include three optical detectors 106, each optical detector 106 positioned in optical communication with each polymer waveguide 126 for detecting a resultant light 130 after the input light 122 travels along each polymer waveguide 126 and through the sample chamber 108. Each optical detector 106 may include a photodiode, an organic photodiode (OPD), a photomultiplier, a CCD detector, a light dependent resistor (LDR), a phototransistor, a photocell for example. Each polymer waveguide 126 may further optically coupled the light input 120 with each optical detector 106.

The sensor element 102 may further include three Bragg grating filters 110, each Bragg grating filter 110 configured to output a predetermined wavelength of the resultant light 130, each Bragg grating filter 110 being positioned in the optical path between each polymer waveguide 126 and each optical detector 106. A transmission spectrum 140 of each Bragg grating filter 110 may behave like a notch filter, while a detected light spectrum 136 (or reflection spectrum) by each optical detector 106 may behave like a band pass filter which may have the centre wavelength as the centre wavelength of absorption wavelength of a target analyte in the sample 124 housed in the sample chamber 108.

In an embodiment, a change in the spectrum of light in the sensor element 102 may be as follows. Firstly, the input light 122 from the light source 104 may include an input light spectrum 128. The resultant light 130 after the input light 122 travels along each polymer waveguide 126 and through the sample chamber 108 may include a resultant light spectrum 132. Then the detected light 134 as seen by each optical detector 106 after the resultant light 130 may be reflected by each Bragg grating filter 110 may include the detected light spectrum 136. Further, the output light 138 after the resultant light 130 may be transmitted across the Bragg grating filter 110 may include a transmission spectrum 140. The total intensity of the detected light spectrum 136 detected by each optical detector 106 may be proportional to the concentration of the target analyte in the sample 124 housed within the sample chamber 108.

In an embodiment, at least a portion of the first contact portion 112 may be positioned outside of the sample chamber 108. The portion of the first contact portion 112 positioned outside of the sample chamber 108 may include two first partial contact portions 142, for example a portion 144 optically coupling the sample chamber 108 to the light source 104 and a portion 146 optically coupling the sample chamber 108 to each Bragg grating filter 110. Each of the first partial contact portions 142 may be the same or different from each other.

In an embodiment, each of the second contact portion 114 may be positioned parallel to each other within the sample chamber 108. Further, each of the second contact portion 114 may be spaced apart by equal or different distance from each other.

The first contact portion 112 may include a continuous portion with a constant diameter. The second contact portion 114 may be configured so as to allow an increased interaction between the input light 122 and the sample 124 as compared to the first contact portion 112. An enlarged view of the optical coupling between the first contact portion 112 and the second contact portion 114 may be as shown.

Further, each second contact portion 114 may include a plurality of shaped portions 116 positioned along a common axis, each shaped portion 116 separated from another shaped portion 116 by a gap 118. Each gap 118 may be spaced at a regular interval along the length of each second contact portion 114. The distance of each gap 118 may be in the range of about 5 µm to about 1 cm, e.g. about 2.5 mm.

Each shaped portion 116 may include a rounded portion and an elongated portion. The rounded portion of one shaped portion 116 may be configured for directing the light onto the elongated portion of another shaped portion 116. The shaped portion 116 may also be of any other suitable shapes depending on user and design requirements.

The sample chamber 108 may include a rectangle shape, a square shape, a circular shape, a triangle shape or any other suitable shapes depending on user and design requirements.

The light source 104 and the three optical detectors 106 may be respectively positioned on two opposite sides of the sample chamber 108. The light source 104 and the three optical detectors 106 may also be positioned on two adjacent sides of the sample chamber 108, depending on user and design requirements.

The sample 124 may include macromolecular biomolecules. The sample 124 may include urine, blood, DNA molecules, proteins, saliva, stool, sweat for example.

The number of the light source 104, the at least one polymer waveguide 126, the shaped portions 116, the optical detector 106 and the Bragg grating filter 110 may vary depending on user and design requirements.

In FIG. 1, light-sample interaction may occur in the at least one polymer waveguide 126. The input light 122 interacts with the sample 124 housed in the sample chamber 108 directly. Light-sample interactions may occur in the plurality of gaps 118 in the second contact portion 114 of the at least one polymer waveguide 126. Input light 122 exiting a first shaped portion 150 at an input side of one gap 118 may be self-focused by the first shaped portion 150 onto the second shaped portion 152 at an output side of the gap 118. The multiple direct interactions between the input light 122 and the sample 124 in the sample chamber 108 may enhance the sensitivity of the sensor element 102.

Figure 2:
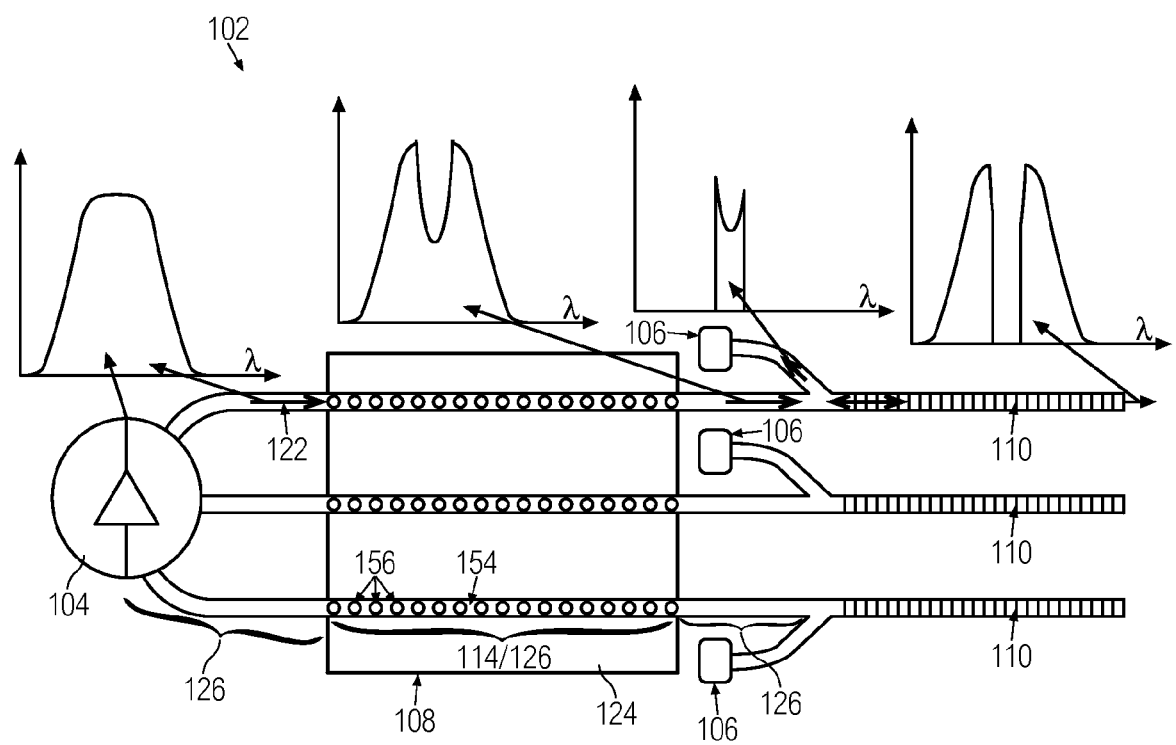
FIG. 2 shows a top view of a sensor element with a light source and three optical detectors respectively positioned on two opposite sides of a sample chamber, three Bragg grating filters and a second contact portion including a continuous portion with at least one hole according to an embodiment.

FIG. 2 shows a top view of a sensor element 102 with a light source 104 and three optical detectors 106 respectively positioned on two opposite sides of a sample chamber 108, three Bragg grating filters 110 and a second contact portion 114 including a continuous portion 154 with at least one hole 156 according to an embodiment.

FIG. 2 may be similar to FIG. 1 except for the difference in structure of the second contact portion 114. In FIG. 2, the second contact portion 114 may include a continuous portion 154 or an elongated portion with a plurality of holes 156, each hole 156 being spaced from another at a regular interval along the length of the continuous portion 154. The holes 156 may also be spaced at a varying interval along the length of the continuous portion 154. The distance between each hole 156 may be in the range of about 100 µm to about 10 cm, e.g. about 2 mm.

There may be between about 1 to about 50 holes 156 along the length of the second contact portion 114, typically about 20 holes 156. Each of the holes 156 may be circular, rectangle, square, triangle in shape or of any other suitable shape. Each hole 156 may be the same or different from each other. The diameter of each hole 156 may be in the range of about 5 µm to about 1 mm, e.g. about 250 µm. Varying the number of holes 156 along the continuous portion 154 may have enhance the sensitivity of the sensor element. The holes 156 serve to enhance the light-sample interactions.

In FIG. 2, light-sample interaction may occur in the at least one polymer waveguide 126. The input light 122 interacts with the sample 124 housed in the sample chamber 108 directly. Light-sample interactions may occur in the plurality of holes 156 in the second contact portion 114 of the at least one polymer waveguide 126. Input light 122 exiting the second contact portion 114 at the holes 156 may be self-coupled back into the at least one polymer waveguide 126. The multiple direct interactions between the input light 122 and the sample 124 in the sample chamber 108 may enhance the sensitivity of the sensor element 102.

Figure 3:
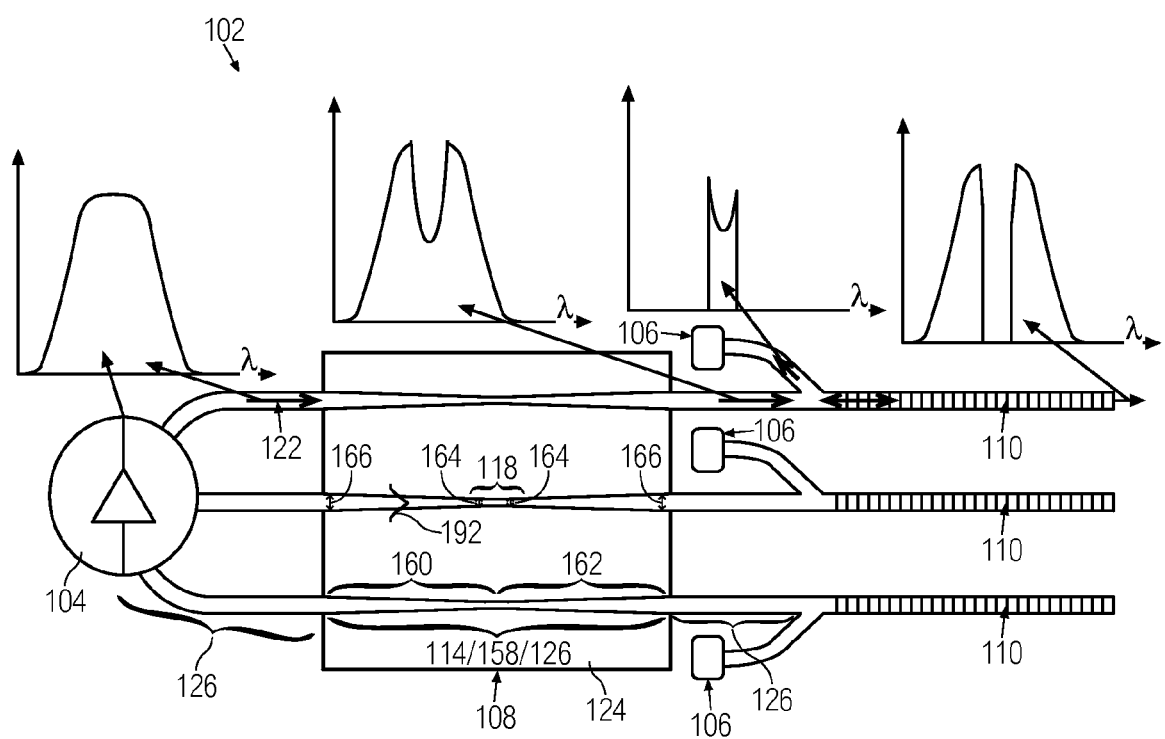
FIG. 3 shows a top view of a sensor element with a light source and three optical detectors respectively positioned on two opposite sides of a sample chamber, three Bragg grating filters and a second contact portion including a continuous portion with a varying diameter according to an embodiment.

FIG. 3 shows a top view of a sensor element 102 with a light source 104 and three optical detectors 106 respectively positioned on two opposite sides of a sample chamber 108, three Bragg grating filters 110 and a second contact portion 114 including a continuous portion 158 with a varying diameter according to an embodiment.

FIG. 3 may be similar to FIG. 1 and FIG. 2 except for the difference in structure of the second contact portion 114. In FIG. 3, the second contact portion 114 may include a continuous portion 158 or an elongated portion with a varying diameter along the length of the second contact portion 114. The diameter may vary according to a predefined pattern along the length of the second contact portion 114 or may just decrease and/or increase along the length of the second contact portion 114. The diameter variation may be in the range of about 5 µm to about 1 mm, e.g. about 300 µm. The length of the elongated portion 158 may also vary depending on user and design requirements. The length of the elongated portion 158 may be in the range of about 500 µm to about 10 cm, typically about 3 cm. The longer the length of the elongated portion 158, the higher the light-sample interaction along the at least one polymer waveguide 126, thereby the better the sensitivity of the sensor element 102.

In FIG. 3, the second contact portion 114 may include a first tapered portion 160 and a second tapered portion 162. The first tapered portion 160 and the second tapered portion 162 may be the same or different from each other. Each of the first tapered portion 160 and the second tapered portion 162 may include a conical portion with a tapered end 164 and an enlarged end 166. The diameter or dimension of the enlarged end 166 may be larger than the tapered end 164. Each of the tapered end 164 of the first tapered portion 160 and the second tapered portion 162 may include a diameter in the range of about 3 µm to about 1 mm, e.g. about 200 µm. Each of the enlarged end 166 of the first tapered portion 160 and the second tapered portion 162 may include a diameter in the range of about 5 µm to about 2 mm, typically about 500 µm.

The first tapered portion 160 may be in optical communication with the second tapered portion 162. By way of example, the tapered end 164 of the first tapered portion 160 and the tapered end 164 of the second tapered portion 162 may be in direct contact with each other so as to form a narrower path or a conical shaped sensing area 168 for the passage of input light 122 as compared to the enlarged end 166 of the respective first 160 and second 162 tapered portions.

In FIG. 3, light-sample interaction may occur outside of the at least one polymer waveguide 126. The input light 122 may interact with the sample 124 housed in the sample chamber 108 via an evanescent field or evanescent wave 192. The light-sample interactions via the evanescent field 192 may be enhanced by the conical shaped sensing area 168 of the at least one polymer waveguide 126. The penetration of the evanescent field 192 depends on the refractive index of the sample 124 housed within the sample chamber 108 and the size of the at least one polymer waveguide 126. The smaller the dimension (e.g. in a plane substantially perpendicular to the light propagation direction of the light within the at least one polymer waveguide) of the at least one polymer waveguide 126, the bigger the penetration depth of the evanescent field 192, thereby the higher the light-sample interaction. Input light 122 exiting the at least one polymer waveguide 126 via the evanescent field 192 may be self-coupled into the at least one polymer waveguide 126. The combination of the enhanced evanescent field 192 and the length of the conical shaped sensing area 168 may enhance the sensitivity of the sensor element 102.

Figure 4:
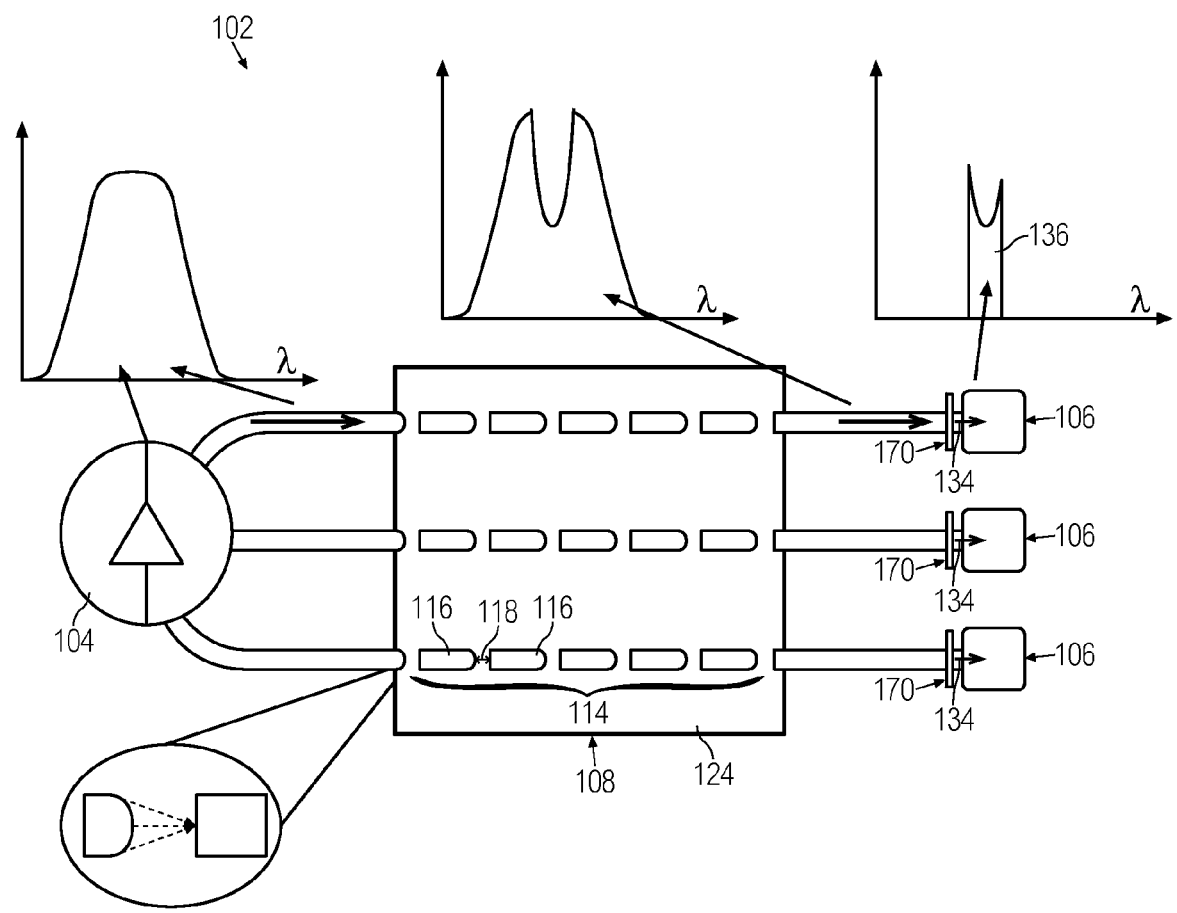
FIG. 4 shows a top view of a sensor element with a light source and three optical detectors respectively positioned on two opposite sides of a sample chamber, three Fabry-Perot filters and a second contact portion including at least two shaped portions, each shaped portion separated by a gap according to an embodiment.

FIG. 4 shows a top view of a sensor element 102 with a light source 104 and three optical detectors 106 respectively positioned on two opposite sides of a sample chamber 108, three Fabry-Perot filters 170 and a second contact portion 114 including at least two shaped portions 116, each shaped portion 116 separated by a gap 118 according to an embodiment.

FIG. 4 may be similar to FIG. 1 except for the difference in the filters adopted. Three Fabry-Perot filters 170 may be adopted in FIG. 4 as compared to three Bragg grating filters 110 adopted in FIG. 1

Each Fabry-Perot filter 170 may behave like a band-pass filter which may have a centre of transmission the same as the centre of absorption of a target analyte in the sample 124 housed in the sample chamber 108. The detected light 134 after passing through each Fabry-Perot filter 170 may include a detected light spectrum 136.

In an embodiment, the total intensity of the detected light spectrum 136 detected by each optical detector 106 may be proportional to the concentration of the target analyte in the sample 124 housed within the sample chamber 108.

Figure 5:
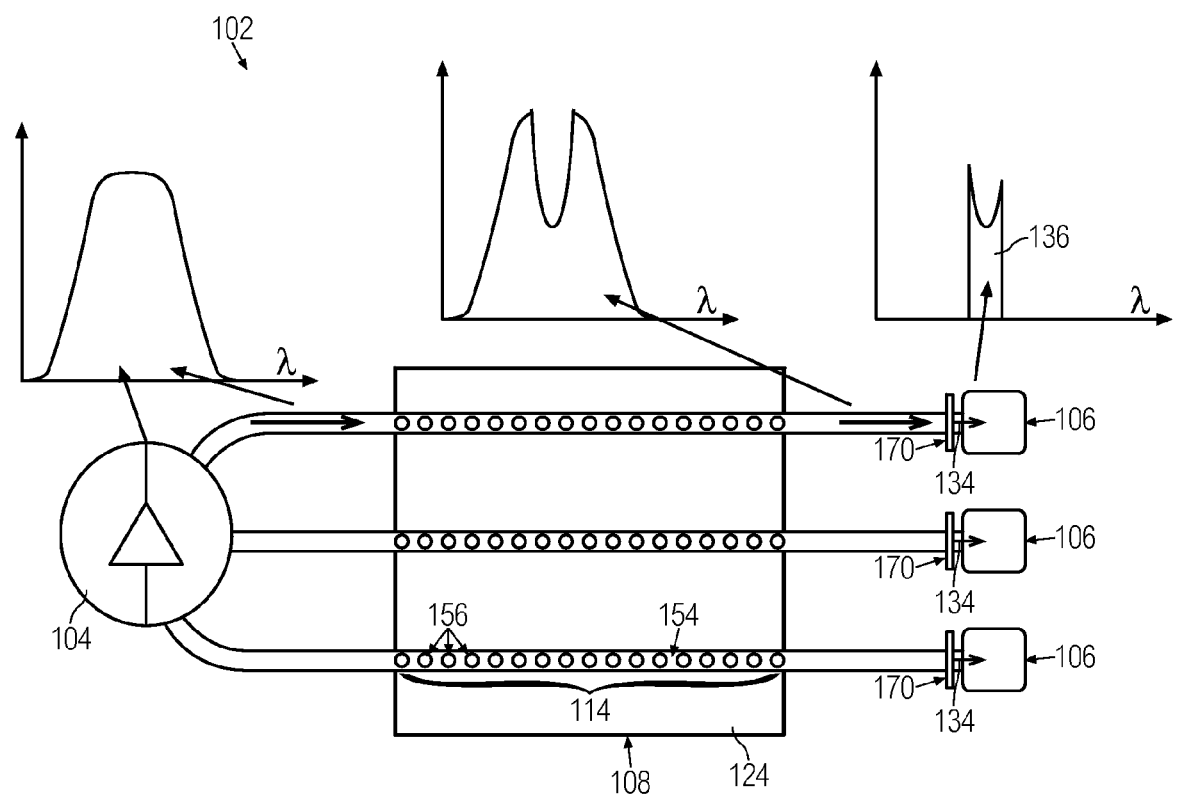
FIG. 5 shows a top view of a sensor element with a light source and three optical detectors respectively positioned on two opposite sides of a sample chamber, three Fabry-Perot filters and a second contact portion including a continuous portion with at least one hole according to an embodiment.

FIG. 5 shows a top view of a sensor element 102 with a light source 104 and three optical detectors 106 respectively positioned on two opposite sides of a sample chamber 108, three Fabry-Perot filters 170 and a second contact portion 114 including a continuous portion 154 with at least one hole 156 according to an embodiment.

FIG. 5 may be similar to FIG. 2 except for the difference in the filters adopted. Three Fabry-Perot filters 170 may be adopted in FIG. 5 as compared to three Bragg grating filters 110 adopted in FIG. 2.

Similarly, each Fabry-Perot filter 170 may behave like a band-pass filter which may have a centre of transmission the same as the centre of absorption of a target analyte in the sample 124 housed in the sample chamber 108. The detected light 134 after passing through each Fabry-Perot filter 170 may include a detected light spectrum 136.

In an embodiment, the total intensity of the detected light spectrum 136 detected by each optical detector 106 may be proportional to the concentration of the target analyte in the sample 124 housed within the sample chamber 108.

Figure 6:
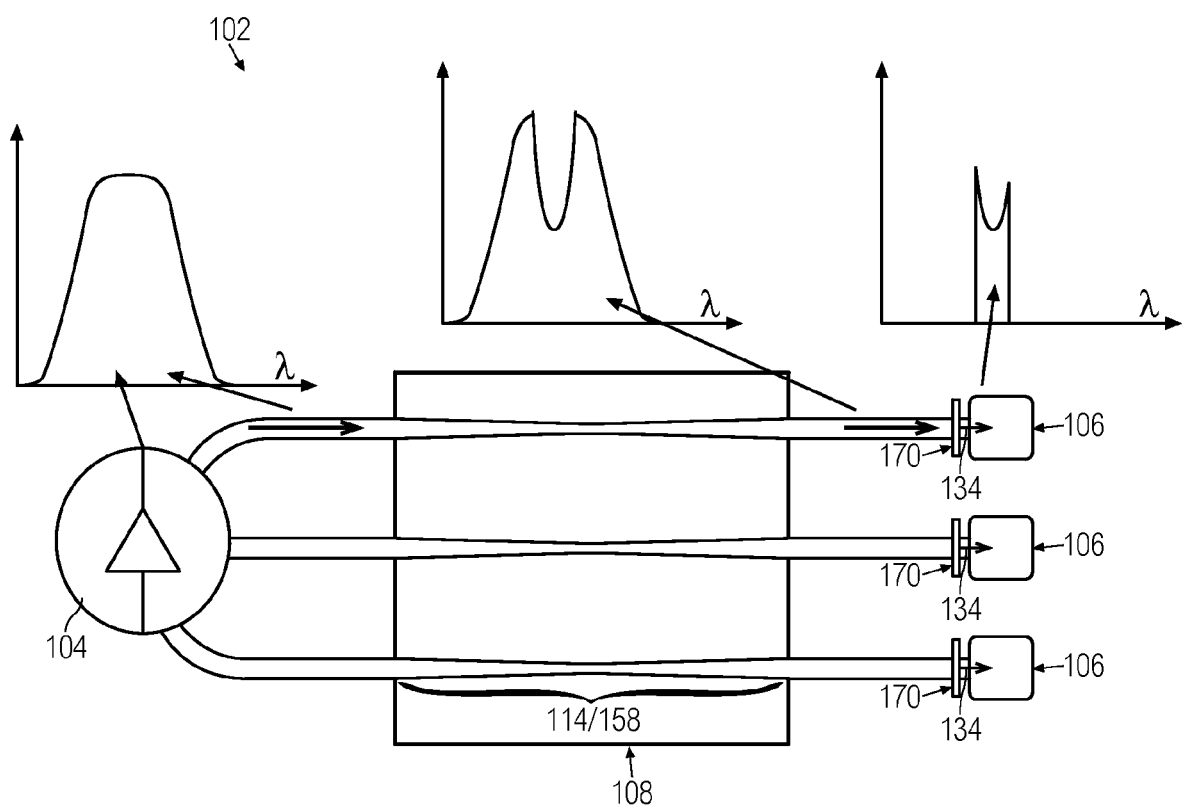
FIG. 6 shows a top view of a sensor element with a light source and three optical detectors respectively positioned on two opposite sides of a sample chamber, three Fabry-Perot filters and a second contact portion including a continuous portion with a varying diameter according to an embodiment.

FIG. 6 shows a top view of a sensor element 102 with a light source 104 and three optical detectors 106 respectively positioned on two opposite sides of a sample chamber 108, three Fabry-Perot filters 170 and a second contact portion 114 including a continuous portion 158 with a varying diameter according to an embodiment.

FIG. 6 may be similar to FIG. 3 except for the difference in the filters adopted. Three Fabry-Perot filters 170 may be adopted in FIG. 6 as compared to three Bragg grating filters 110 adopted in FIG. 3.

Similarly, each Fabry-Perot filter 170 may behave like a band-pass filter which may have a centre of transmission the same as the centre of absorption of a target analyte in the sample 124 housed in the sample chamber 108. The detected light 134 after passing through each Fabry-Perot filter 170 may include a detected light spectrum 136.

In an embodiment, the total intensity of the detected light spectrum 136 detected by each optical detector 106 may be proportional to the concentration of the target analyte in the sample 124 housed within the sample chamber 108.

Figure 7:
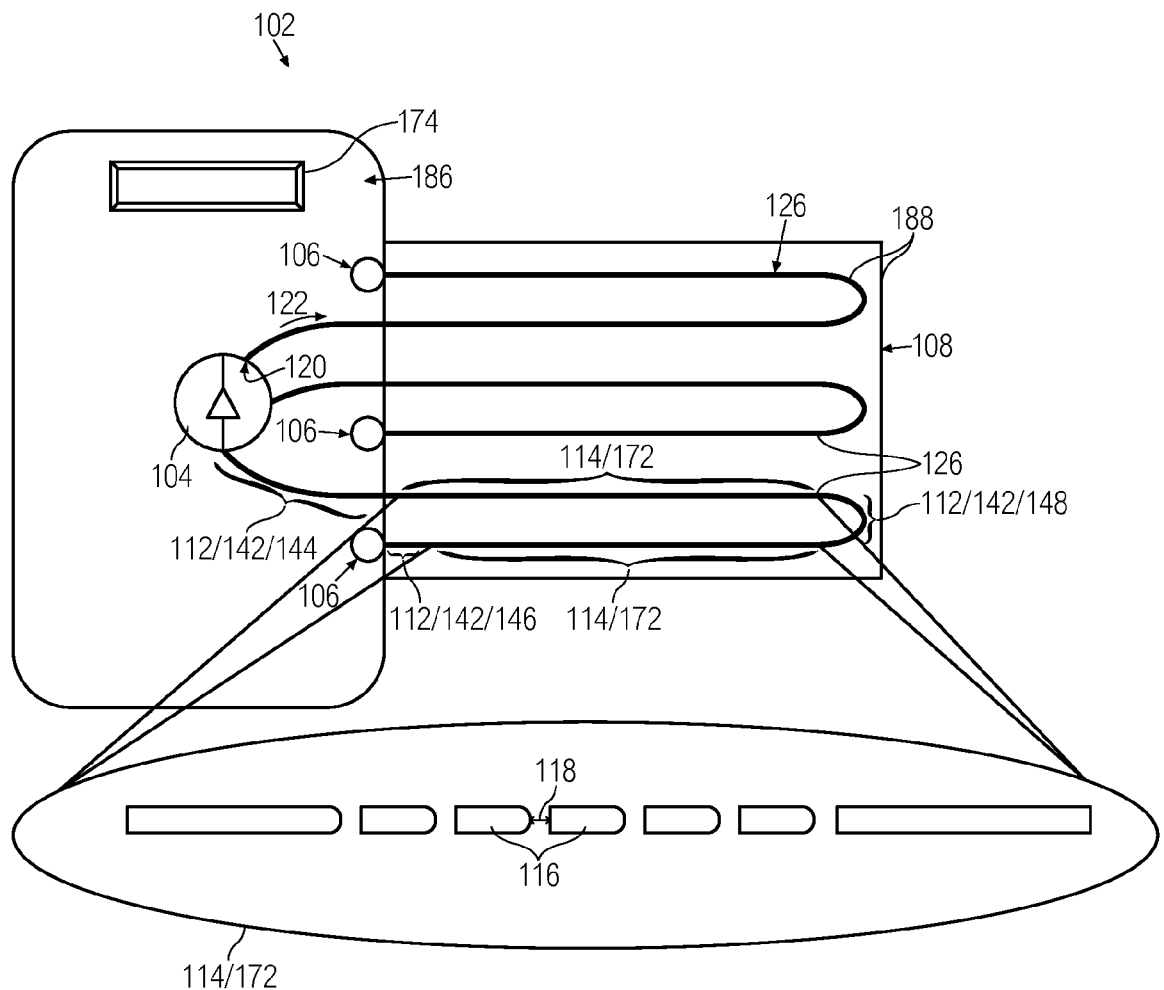
FIG. 7 shows a top view of a sensor element with a light source and three optical detectors respectively positioned on a same side of a sample chamber and a second contact portion including at least two shaped portions, each shaped portion separated by a gap according to an embodiment.

FIG. 7 shows a top view of a sensor element 102 with a light source 104 and three optical detectors 106 respectively positioned on a same side of a sample chamber 108 and a second contact portion 114 including at least two shaped portions 116, each shaped portion 116 separated by a gap 118 according to an embodiment.

FIG. 7 may be similar to FIG. 1 except for the difference in the arrangement of the light source 104 and the optical detector 106 and the absence of the Bragg grating filters 110. In FIG. 7, the Bragg grating filters 110 or any other types of filters may or may not be present in the sensor element 102.

In FIG. 7, the sensor element 102 may include a light input 120 configured to receive input light 122, a sample chamber 108 configured to accommodate a sample 124 and three polymer waveguides 126 optically coupling the light input 120 with the sample chamber 108, each of the three polymer waveguides 126 including a first contact portion 112 and a second contact portion 114, wherein at least a portion of the second contact portion 114 may be arranged in the sample chamber 108. The second contact portion 114 may include a different structure than the first contact portion 112 so that a change of the light intensity of the input light 122 passing through the second contact portion 114 may be caused due to an interaction between the input light 122 passing through the second contact portion 114 and the sample 124 and wherein the change of the light intensity of the input light 122 passing through the second contact portion 114 may be different from the change of the light intensity of the input light 122 passing through the first contact portion 112.

The sensor element 102 further includes a light source 104 configured to provide the input light 122 to the light input 120. The light source 104 may include a laser, a white light, a fluorescent light, a laser diode, a light emitting diode (LED), an organic LED (OLED), a gas discharge light source, an incandescent lamp, an electroluminescent lamp for example.

The sensor element 102 may further include three optical detectors 106, each optical detector 106 positioned in optical communication with each polymer waveguide 126 for detecting a resultant light 130 after the input light 122 travels along each polymer waveguide 126 and through the sample chamber 108. Each optical detector 106 may include a photodiode, a photomultiplier, a CCD detector, a light dependent resistor (LDR), a phototransistor, a photocell for example. Each polymer waveguide 126 may further optically coupled the light input 120 with each optical detector 106.

In an embodiment, a portion of the three polymer waveguides 126 may be positioned in the sample chamber 108. This may imply that a portion of the first contact portion 112 and the second contact portion 114 may be arranged in the sample chamber 108. Each of the three polymer waveguides 126 may be configured so as to direct the input light 122 back onto the same side of the sample chamber 108 as the light source 104. Each of the three polymer waveguides 126 may be U-shaped or any other suitable shape. Further, each of the three polymer waveguides 126 may be positioned parallel to each other within the sample chamber 108.

The second contact portion 114 may include two second partial contact portions 172. The first contact portion 112 may include three first partial contact portions 142, for example a portion 144 optically coupling the sample chamber 108 to the light source 104, a portion 146 optically coupling the sample chamber 108 to each optical detector 106 and a portion 148 optically coupling the two second partial contact portions 172. Each of the first partial contact portions 142 may be the same or different from each other. Further, each of the second partial contact portions 172 may be the same or different from each other.

The first contact portion 112 or each first partial contact portion 142 may include a continuous portion with a constant diameter. The second contact portion 114 or each second partial contact portion 172 may be configured so as to allow an increased interaction between the input light 122 and the sample 124 as compared to the first contact portion 112. An enlarged view of the second contact portion 114 may be as shown.

From the enlarged view, each second contact portion 114 or each second partial contact portion 172 may include a plurality of shaped portions 116 positioned along a common axis, each shaped portion 116 separated from another shaped portion 116 by a gap 118. Each gap 118 may be spaced at a regular interval along the length of each second contact portion 114. The distance of each gap 118 may be in the range of about 5 $\mu$m to about 1 cm, e.g. about 2.5 mm Each shaped portion 116 may include a rounded portion and an elongated portion. The rounded portion of one shaped portion 116 may be configured for directly the light onto the elongated portion of another shaped portion 116. The shaped portion 116 may also be of any other suitable shapes depending on user and design requirements.

The sample chamber 108 may include a rectangle shape, a square shape, a circular shape, a triangle shape or any other suitable shapes depending on user and design requirements.

In an embodiment, the light source 104 and the three optical detectors 106 may be positioned on a same side of the sample chamber 108. The light source 104 and the three optical detectors 106 may also be positioned on any suitable side of the sample chamber 108, depending on user and design requirements.

In an embodiment, the sensor element 102 further include a display unit 174 for displaying the concentration of the target analyte within the sample 124. The dimensions of the display unit 174 may vary depending on user and design requirements. The number of the display unit 174 may correspond to the number of the at least one optical detector 106.

In an embodiment, the sensor element 102 may include an electronics system (not shown) such that the electrical output of each of the at least one optical detector 106 may be amplified, filtered, processed and displayed quantitively or semiquantitatively. Therefore, the concentration of the target analyte housed in the sample chamber 108 may be obtained quantitively or semiquantitatively and displayed in the display unit 174.

In an embodiment, the light source 104, the three optical detectors 106 and the display unit 174 may be arranged in a first device 186. The dimensions of the first device 186 may include a height of about 0.5 cm to about 10 cm, e.g. about 5 cm, a breadth of about 0.5 cm to about 20 cm, e.g. about 10 cm and a length of about 2 cm to about 30 cm, e.g. about 10 cm. The first device 186 may include a polymer material, metals and glasses for example. The first device 186 may also include other electronic components.

In an embodiment, the sample chamber 108 and three polymer waveguides 126 may be arranged in a second device 188. The dimensions of the second device 188 may include a height of about 100 $\mu$m to about 5 cm, e.g. about 1 cm, a breadth of about 1 mm to about 10 cm, e.g. about 1 cm and a length of about 1 cm to about 25 cm, e.g. about 6.5 cm. The second device 188 may include a polymer material, glass, metals, silicon (Si) for example.

In an embodiment, the dimensions of the first device 186 may be comparable to or different from the dimensions of the second device 188. The material of the first device 186 may be the same or different from the material of the second device 188.

In an embodiment, the second device 188 may be detachably coupled from the first device 186 through the concept of plug-and-play. The first device 186 may be a permanent instrument system and the second device 188 may be a disposable unit.

The sample 124 may include macromolecular biomolecules. The sample 124 may include urine, blood, saliva, stool and sweat for example.

The number of the light source 104, the display unit 174, the at least one polymer waveguide 126, the shaped portions 116 and the at least one optical detector 106 may vary depending on user and design requirements.

In FIG. 7, light-sample interaction may occur in the at least one polymer waveguide 126. The input light 122 interacts with the sample 124 housed in the sample chamber 108 directly. Light-sample interactions may occur in the plurality of gaps 118 in the second contact portion 114 of the at least one polymer waveguide 126. Input light 122 exiting a first shaped portion 116 at an input side of one gap 118 may be self-focused by the first shaped portion 150 onto the second shaped portion 152 at an output side of the gap 118. The multiple direct interactions between the input light 122 and the sample 124 in the sample chamber 108 may enhance the sensitivity of the sensor element 102.

Figure 8:
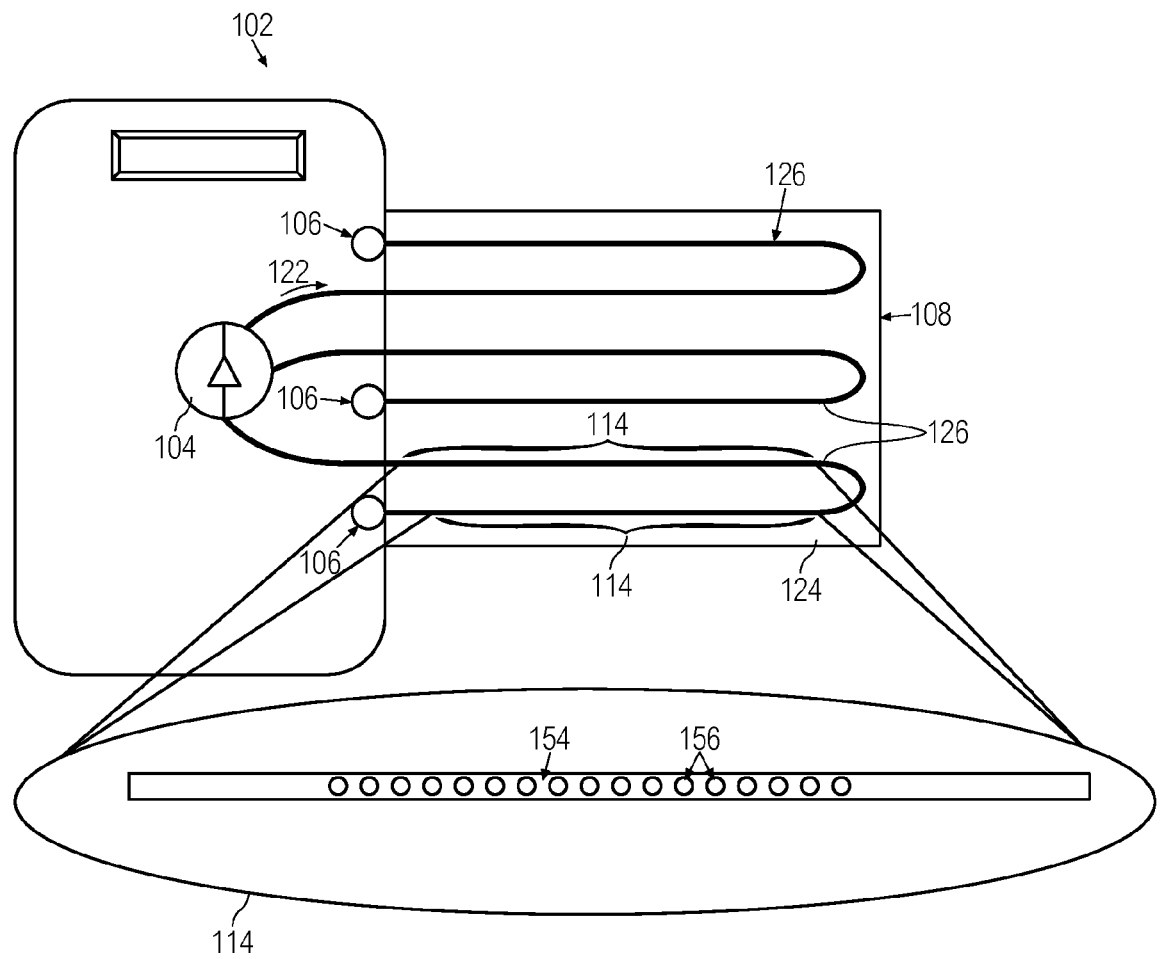
FIG. 8 shows a top view of a sensor element with a light source and three optical detectors respectively positioned on a same side of a sample chamber and a second contact portion including a continuous portion with at least one hole according to an embodiment.

FIG. 8 shows a top view of a sensor element 102 with a light source 104 and three optical detectors 106 respectively positioned on a same side of a sample chamber 108 and a second contact portion 114 including a continuous portion 154 with at least one hole 156 according to an embodiment.

FIG. 8 may be similar to FIG. 7 except for the difference in structure of the second contact portion 114. In FIG. 8, the second contact portion 114 may include a continuous portion 154 or an elongated portion with a plurality of holes 156, each hole 156 being spaced from another at a regular interval along the length of the continuous portion 154. The holes 156 may also be spaced at a varying interval along the length of the continuous portion 154. The distance between each hole 156 may be in the range of about 100 μm to about 10 cm, e.g. about 2 mm.

There may be in the range from about 1 to about 50 holes 156 along the length of the second contact portion 114, e.g. in the range from about 1 to about 30 holes 156, e.g. in the range from about 1 to about 20 holes 156. Each of the holes 156 may be circular, rectangle, square, triangle in shape or of any other suitable shape. The diameter of each hole 156 may be in the range of about 5 μm to about 1 mm, typically about 250 μm. Varying the number of holes 156 along the continuous portion 154 may have enhance the sensitivity of the sensor element. The holes 156 serve to enhance the light-sample interactions.

In FIG. 8, light-sample interaction may occur in the at least one polymer waveguide 126. The input light 122 interacts with the sample 124 housed in the sample chamber 108 directly. Light-sample interactions may occur in the plurality of holes 156 in the second contact portion 114 of the at least one polymer waveguide 126. Input light 122 exiting the second contact portion 114 at the holes 156 may be self-coupled back into the waveguides. The multiple direct interactions between the input light 122 and the sample 124 in the sample chamber 108 may enhance the sensitivity of the sensor element 102.

Figure 9:
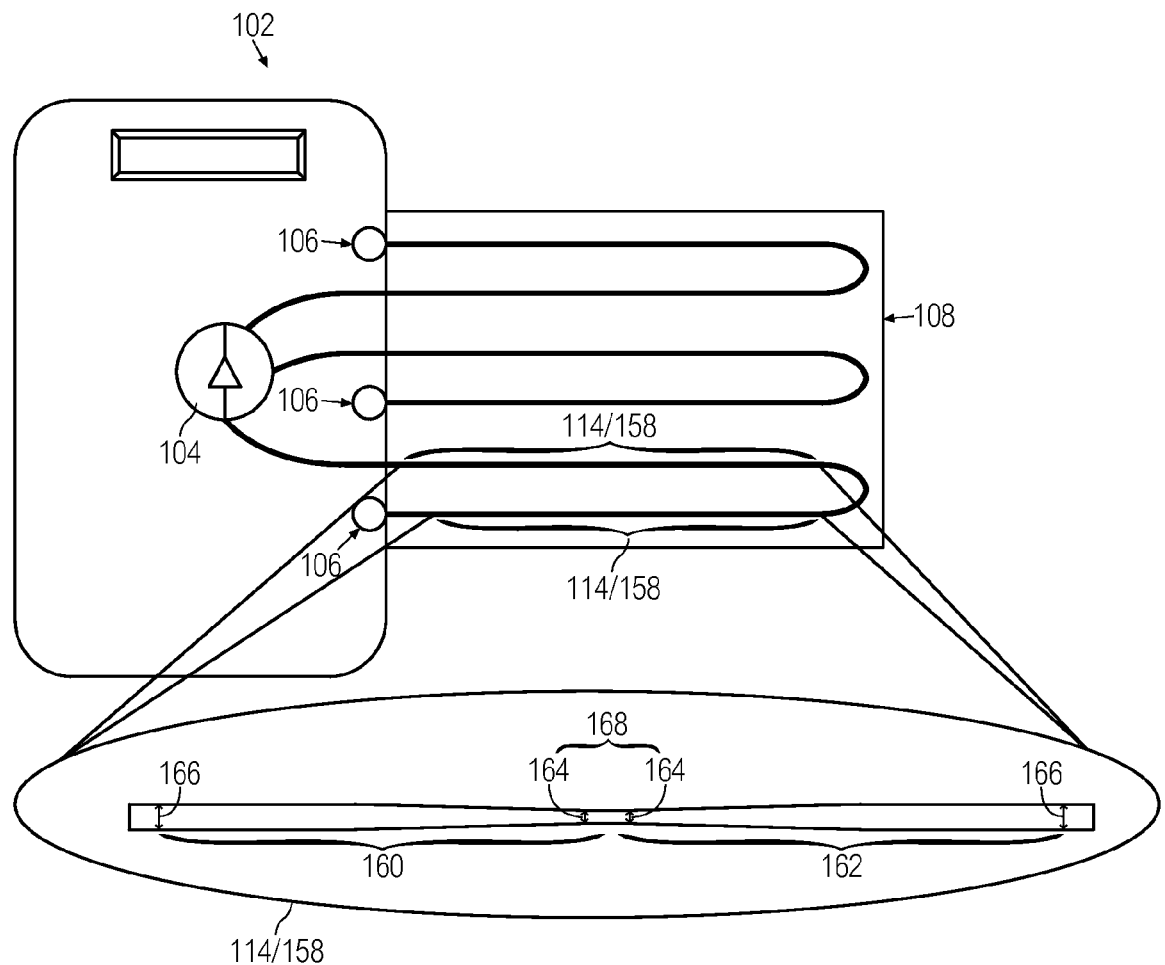
FIG. 9 shows a top view of a sensor element with a light source and three optical detectors respectively positioned on a same side of a sample chamber and a second contact portion including a continuous portion with a varying diameter according to an embodiment.

FIG. 9 shows a top view of a sensor element 102 with a light source 104 and three optical detectors 106 respectively positioned on a same side of a sample chamber 108 and a second contact portion 114 including a continuous portion 158 with a varying diameter according to an embodiment.

FIG. 9 may be similar to FIG. 7 and FIG. 8 except for the difference in structure of the second contact portion 114. In FIG. 9, the second contact portion 114 may include a continuous portion 158 or an elongated portion with a varying diameter along the length of the second contact portion 114. The diameter may vary according to a predefined pattern along the length of the second contact portion 114 or may just decrease and/or increase along the length of the second contact portion 114. The diameter variation may be in the range of about 5 μm to about 1 mm, e.g. about 300 μm. The length of the elongated portion 158 may also vary depending on user and design requirements. The length of the elongated portion 158 may be in the range of about 500 μm to about 10 cm, e.g. about 3 cm. The larger the length of the elongated portion 158, the higher the light-sample interaction along the at least one polymer waveguide 126, thereby the better the sensitivity of the sensor element 102.

In FIG. 9, the second contact portion 114 may include a first tapered portion 160 and a second tapered portion 162. The first tapered portion 160 and the second tapered portion 162 may be the same or different from each other. Each of the first tapered portion 160 and the second tapered portion 162 may include a conical portion with a tapered end 164 and an enlarged end 166. The diameter or dimension of the enlarged end 166 may be larger than the tapered end 164. Each of the tapered end 164 of the first tapered portion 160 and the second tapered portion 162 may include a diameter in the range of about 3 μm to about 1 mm, e.g. about 200 μm. Each of the enlarged end 166 of the first tapered portion 160 and the second tapered portion 162 may include a diameter in the range of about 5 μm to about 2 mm, e.g. about 500 μm.

The first tapered portion 160 may be in optical communication with the second tapered portion 162. The tapered end 164 of the first tapered portion 160 and the tapered end 164 of the second tapered portion 162 may be in direct contact with each other so as to form a narrower path or a conical shaped sensing area 168 for the passage of input light 122 as compared to the enlarged end 166 of the respective first 160 and second 162 tapered portions.

In FIG. 9, light-sample interaction may occur outside of the at least one polymer waveguide 126. The input light 122 interacts with the sample 124 housed in the sample chamber 108 via evanescent field. The light-sample interactions via the evanescent field may be enhanced by the conical shaped sensing area 168 of the at least one polymer waveguide 126. The penetration of the evanescent field depends on the refractive index of the sample 124 housed within the sample chamber 108 and the size of the at least one polymer waveguide 126. The smaller the dimension of the at least one polymer waveguide 126, the bigger the penetration depth of the evanescent field, thereby the higher the light-sample interaction. Input light 122 exiting the at least one polymer waveguide 126 via the evanescent field may be self-coupled into the at least one polymer waveguide 126. The combination of the enhanced evanescent field and the length of the conical shaped sensing area 168 may enhance the sensitivity of the sensor element 102.

Figure 10:
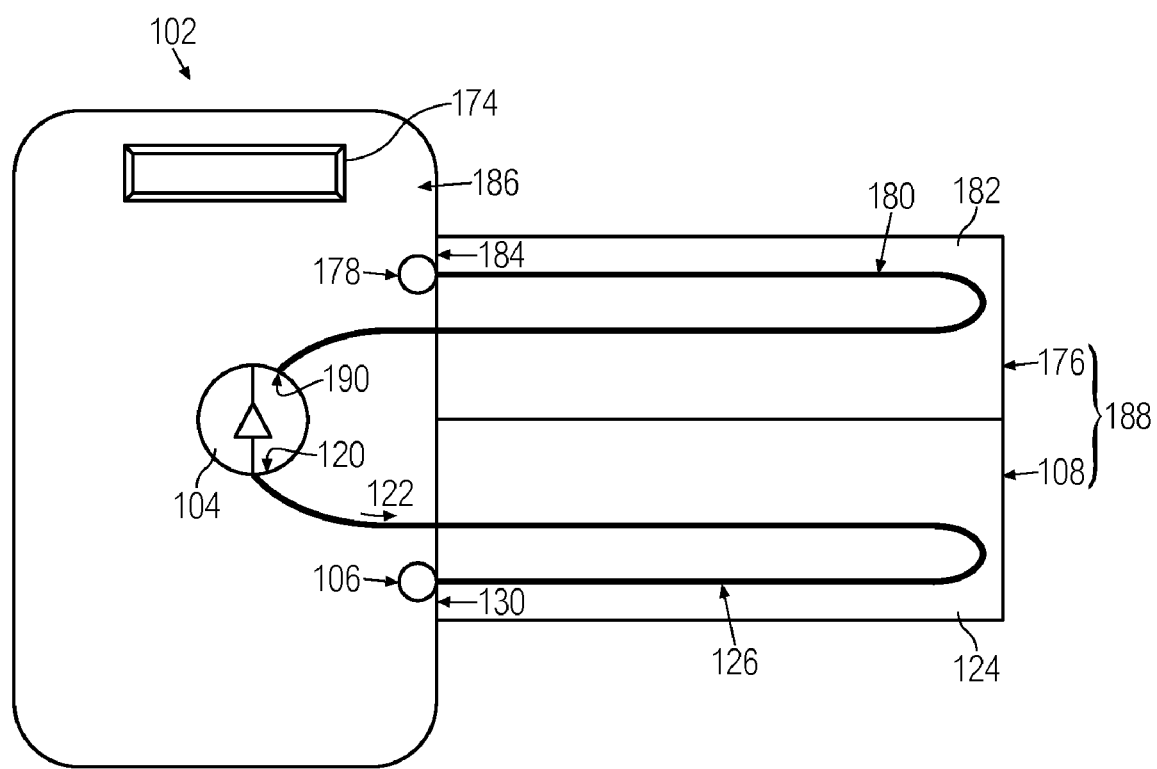
FIG. 10 shows a top view of a sensor element including a further sample chamber, a further polymer waveguide and a further optical detector, the sensor element with a light source, one optical detector and the further optical detector respectively positioned on a same side of a sample chamber and the further sample chamber according to an embodiment.

FIG. 10 shows a top view of a sensor element 102 including a further sample chamber 176, a further polymer waveguide 180 and a further optical detector 178, the sensor element 102 with a light source 104, one optical detector 106 and the further optical detector 178 respectively positioned on a same side of a sample chamber 108 and the further sample chamber 176 according to an embodiment.

FIG. 10 may be similar to FIG. 7 except that the sensor element 102 further include a further sample chamber 176, a further polymer waveguide 180 and a further optical detector 106.

In FIG. 10, the sensor element 102 may include a light input 120 configured to receive input light 122, a sample chamber 108 configured to accommodate a sample 124 and one polymer waveguide 126 optically coupling the light input 120 with the sample chamber 108.

The sensor element 102 further includes a light source 104 configured to provide the input light 122 to the light input 120. The light source 104 may include a laser, a white light, a fluorescent light, a laser diode, a light emitting diode (LED), an organic LED, a gas discharge light source, a incandescent lamp, and an electroluminescent lamp. for example.

The sensor element 102 may further include one optical detector 106, the optical detector 106 positioned in optical communication with the polymer waveguide 126 for detecting a resultant light 130 after the input light 122 travels along the polymer waveguide 126 and out from the sample chamber 108. The optical detector 106 may include a photodiode, an organic photodiode, a photomultiplier, a CCD detector, a light dependent transistor (LDR), a phototransistor and a photocell for example. The polymer waveguide 126 may further optically coupled the light input 120 with the optical detector 106.

In an embodiment, the polymer waveguide 126 may be positioned in the sample chamber 108. The polymer waveguide 126 may be configured so as to direct the input light 122 back onto the same side of the sample chamber 108 as the light source 104.

The polymer waveguide 126 may include any of the structures as mentioned in FIG. 1 to FIG. 6.

The sample chamber 108 may include a rectangle shape, a square shape, a circular shape, a triangle shape or any other suitable shapes depending on user and design requirements.

In an embodiment, the sensor element 102 may further include a further sample chamber 176 configured to accommodate a further sample 182. The further sample chamber 176 may be the same or different from the sample chamber 108. There may be more than one further sample chambers 176. The number of the sample chamber 108 or the further sample chamber 176 may depend on user and design requirements. The further sample chamber 176 may be positioned adjacent to the sample chamber 108.

In an embodiment, the further sample 182 may be the same or different from the sample 124. By way of example, either the sample 124 or the further sample 182 may be the reference sample while the other may be the sample or analyte of interest. The sample 124 may include macromolecular biomolecules, molecules of interest or target analyte. The sample 124 may include urine, blood, DNA molecules, proteins, blood, saliva, stool and sweat for example.

In an embodiment, the sensor element 102 may further include a further polymer waveguide 180 optically coupling the further sample chamber 176 with the further light input 190. There may be more than one further polymer waveguide 180. The number of the polymer waveguide 126 or the further polymer waveguide 180 may depend on user and design requirements. The light input 120 and the further light input 190 may be the same or different.

In an embodiment, at least a portion of the further polymer waveguide 180 may be arranged in the further sample chamber 176.

In an embodiment, the further polymer waveguide 180 may be the same or different from the at least one polymer waveguide 126. The further polymer waveguide 180 may also include any of the structures as mentioned in FIG. 1 to FIG. 6.

In an embodiment, the sensor element 102 may further include a further optical detector 178, the further optical detector 178 may be positioned in optical communication with the further polymer waveguide 180 for detecting a further resultant light 184 after the input light 122 travels along the further polymer waveguide 180 and out from the further sample chamber 176.

In an embodiment, the further optical detector 178 may be the same or different from the at least one optical detector 106. The number of the optical detector 106 and the further optical detector 178 may vary depending on user and design requirements.

In an embodiment, the sensor element 102 may further include a display unit 174 for displaying the concentration of the target analyte within the sample 124. The dimensions of the display unit 174 may vary depending on user and design requirements. The number of the display units 174 may correspond to the number of optical detectors 106.

In an embodiment, the light source 104, the display unit 174, the optical detector 106 and the further optical detector 178 may be positioned on a same side of the sample chamber 108 and the further sample chamber 176. The light source 104, the display unit 174, the optical detector 106 and the further optical detector 178 may also be positioned on any other suitable sides of the sample chamber 108 and the further sample chamber 176, depending on user and design requirements.

In an embodiment, the light source 104, the optical detector 106, the further optical detector 178 and the display unit 174 may be arranged or housed in the first device 186. The dimensions of the first device 186 may include a height of about 0.5 cm to about 10 cm, e.g. about 5 cm, a breadth of about 0.5 cm to about 20 cm, e.g. about 10 cm and a length of about 2 cm to about 30 cm, e.g. about 10 cm. The first device 186 may include a polymer material, metal, glass for example. The first device 186 may also include other electronic components.

In an embodiment, the sample chamber 108, the polymer waveguide 126, the further sample chamber 176 and the further polymer waveguide 180 may be arranged or housed in the second device 188. The dimensions of the second device 188 may include a height of about 100 μm to about 5 cm, e.g. about 1 cm, a breadth of about 1 mm to about 10 cm, e.g. about 1 cm and a length of about 1 cm to about 25 cm, e.g. about 6.5 cm. The second device 188 may include a polymer material for example.

In an embodiment, the sample chamber 108 and the at least polymer waveguide 126 may be arranged or housed in one device and the further sample chamber 176 and the further polymer waveguide 180 may be arranged or housed in another device In an embodiment, the dimensions of the first device 186 may be comparable to or different from the dimensions of the second device 188. The material of the first device 186 may be the same or different from the material of the second device 188.

In an embodiment, the second device 188 may be detachably coupled from the first device 186 through the concept of plug-and-play.

In an embodiment, the number and position of the light source 104, the display unit 174, the polymer waveguide 126, the further polymer waveguide 180, the optical detector 106, the further optical detector 178, the sample chamber 108, the further sample chamber 176 may vary depending on user and design requirements.

In an embodiment, the resultant light 130 after the input light 122 travels along the polymer waveguide 126 and through the sample chamber 108 may include a resultant light spectrum (not shown). The further resultant light 184 after the input light 122 travels along the further polymer waveguide 180 and through the further sample chamber 176 may include a further resultant light spectrum (not shown). Assuming that the sample chamber 108 contains the reference sample and the further sample chamber 176 contains the analyte of interest, the further resultant light spectrum may need to be corrected by the resultant light spectrum which may act as the reference signal, so that the electrical signals processed by the electronic system housed within the first device 186 may be purely signals affected by the analyte of interest.

Figure 11:
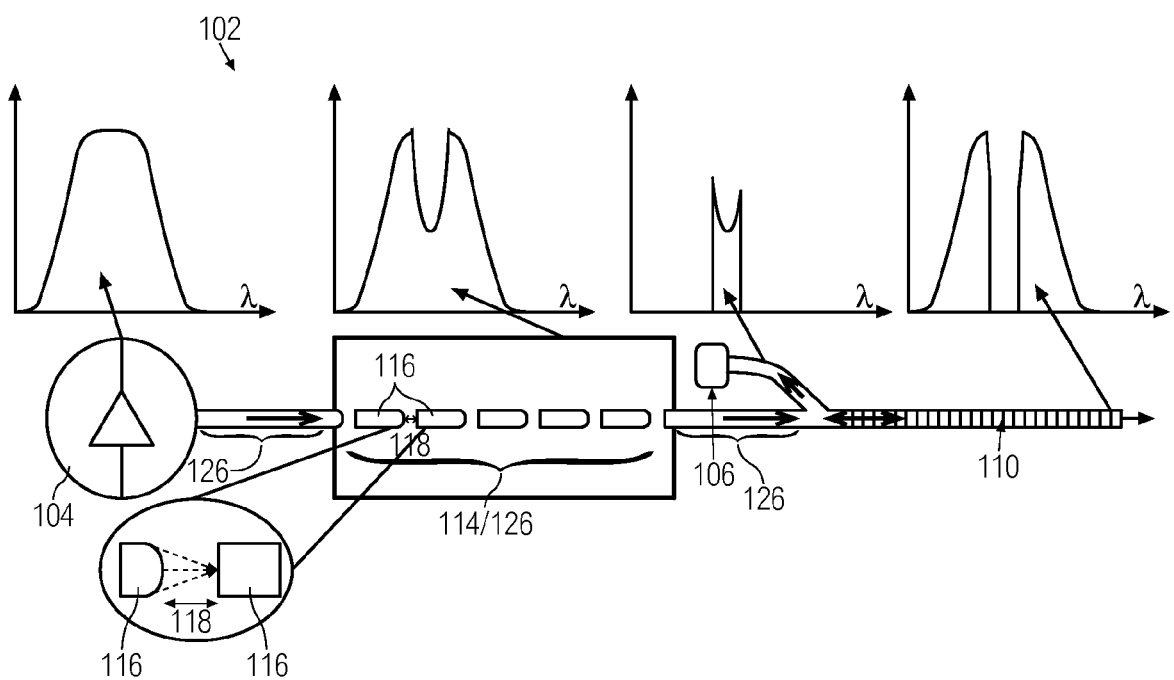
FIG. 11 shows a top view of a sensor element with a light source and one optical detector respectively positioned on two opposite sides of a sample chamber, one Bragg grating filter and a second contact portion including at least two shaped portions, each shaped portion separated by a gap according to an embodiment.

FIG. 11 shows a top view of a sensor element 102 with a light source 104 and one optical detector 106 respectively positioned on two opposite sides of a sample chamber 108, one Bragg grating filter 110 and a second contact portion 114 including at least two shaped portions 116, each shaped portion 116 separated by a gap 118 according to an embodiment.

FIG. 11 may be similar to FIG. 1 except for the difference in the number of polymer waveguide 126, optical detector 106 and Bragg grating filter 110. FIG. 11 shows one polymer waveguide 126, one optical detector 106 and one Bragg grating filter 110 while FIG. 1 shows three polymer waveguides 126, three optical detectors 106 and three Bragg grating filters 110. The polymer waveguide 126 may also include any of the structures as mentioned in FIG. 1 to FIG. 6.

Figure 12:
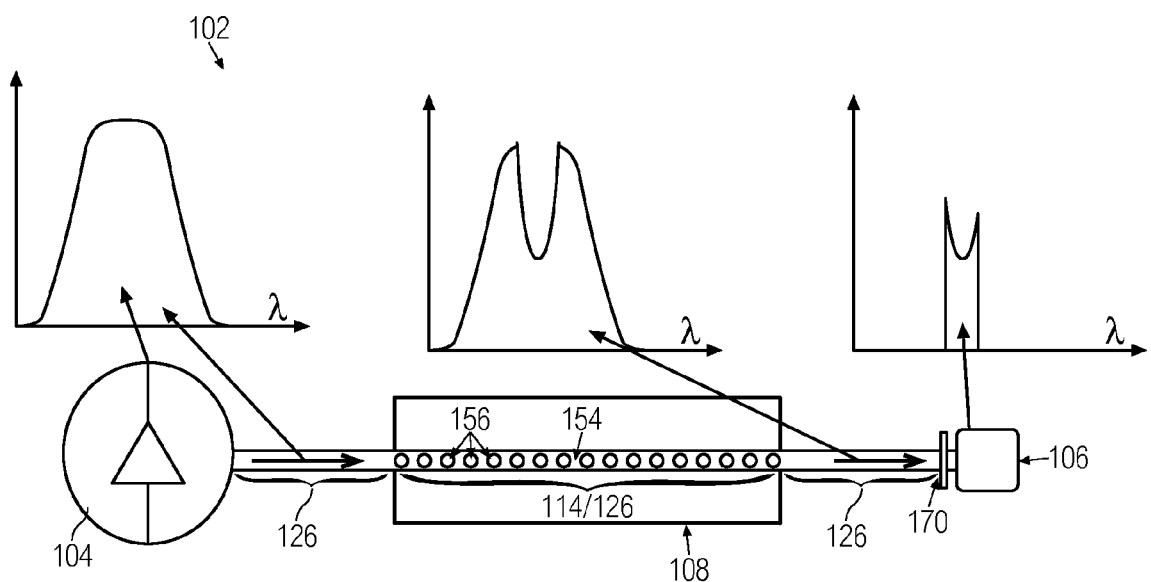
FIG. 12 shows a top view of a sensor element with a light source and one optical detector respectively positioned on two opposite sides of a sample chamber, one Fabry-Perot filter and a second contact portion including a continuous portion with at least one hole according to an embodiment.

FIG. 12 shows a top view of a sensor element 102 with a light source 104 and one optical detector 106 respectively positioned on two opposite sides of a sample chamber 108, one Fabry-Perot filter 170 and a second contact portion 114 including a continuous portion 154 with at least one hole 156 according to an embodiment.

FIG. 12 may be similar to FIG. 5 except for the difference in the number of polymer waveguide 126, optical detector 106 and Fabry-Perot filter 110. FIG. 12 shows one polymer waveguide 126, one optical detector 106 and one Fabry-Perot filter 170 while FIG. 5 shows three polymer waveguides 126, three optical detectors 106 and three Fabry-Perot filters 170. The polymer waveguide 126 may also include any of the structures as mentioned in FIG. 1 to FIG. 6.

Figure 13:
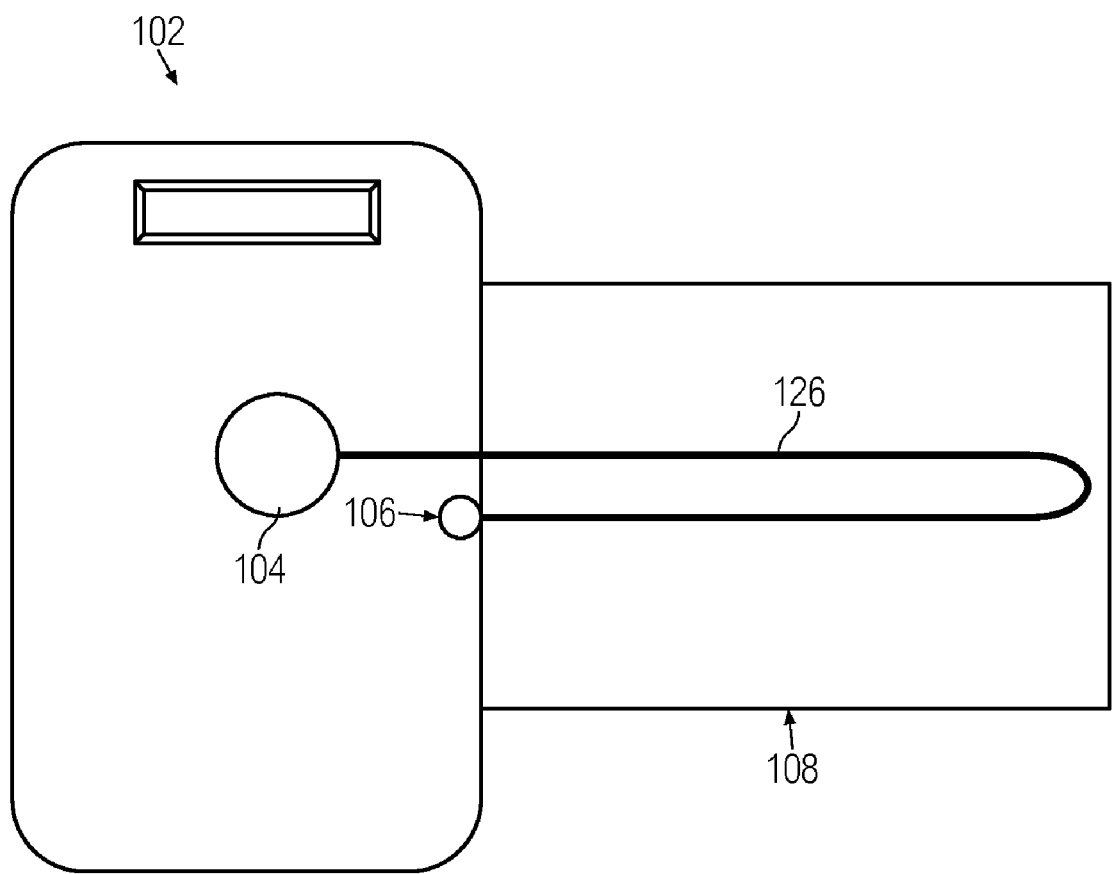
FIG. 13 shows a top view of a sensor element with a light source and one optical detector respectively positioned on a same side of a sample chamber according to an embodiment.

FIG. 13 shows a top view of a sensor element 102 with a light source 104 and one optical detector 106 respectively positioned on a same side of a sample chamber 108 according to an embodiment.

FIG. 13 may be similar to FIG. 7 except for the difference in the number of polymer waveguide 126 and optical detector 106. FIG. 13 shows one polymer waveguide 126 and one optical detector 106 while FIG. 7 shows three polymer waveguides 126 and three optical detectors 106. The polymer waveguide 126 may also include any of the structures as mentioned in FIG. 7, FIG. 8 and FIG. 9.

The polymer waveguide 126 may include any of the structures as mentioned in FIG. 1 to FIG. 6.

Figure 14:
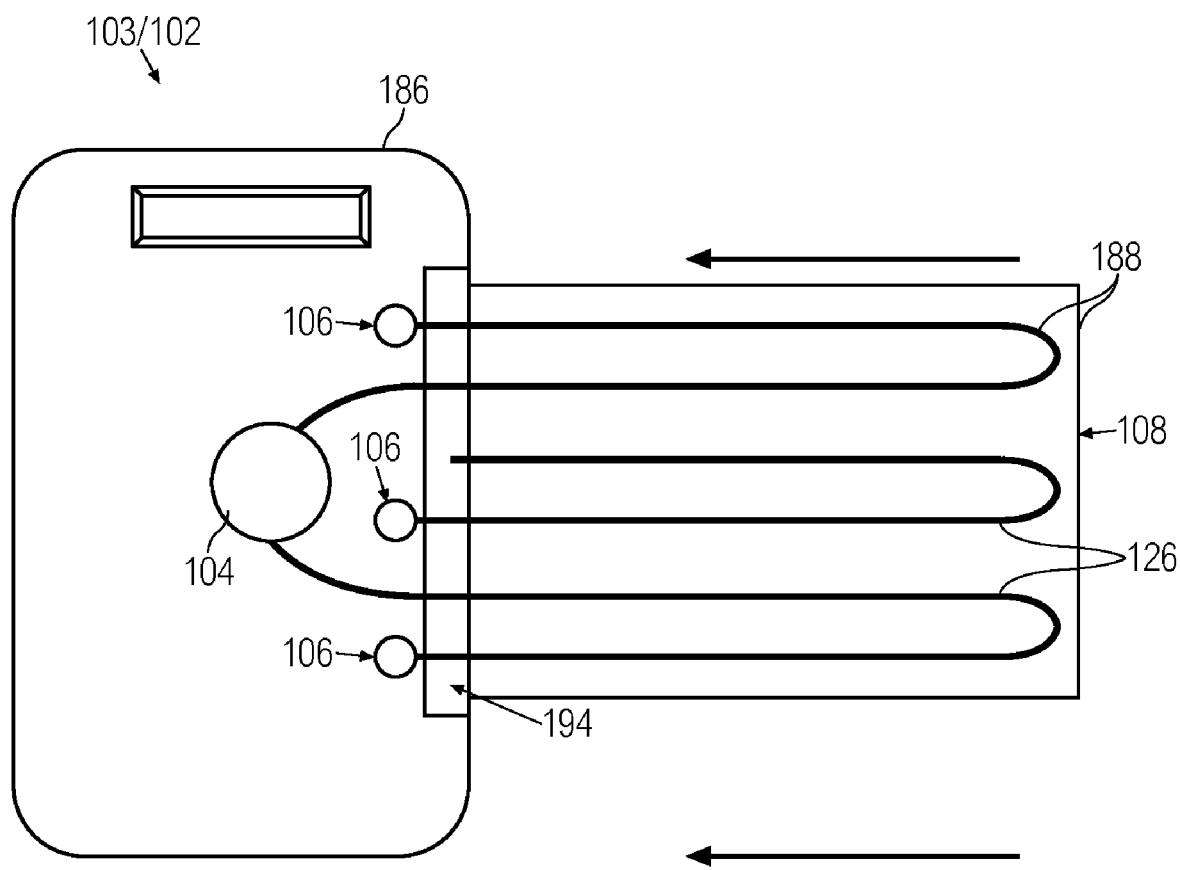
FIG. 14 shows a top view of a sensor arrangement including a sensor element with one light source, three optical detectors, a sample chamber and three polymer waveguides, a first device including the light source and the three optical detectors and a second device including the sample chamber and three polymer waveguides, wherein the second device is detachably coupled with the first device via a socket coupling according to an embodiment.

FIG. 14 shows a top view of a sensor arrangement 103 including a sensor element 102 with one light source 104, three optical detectors 106, a sample chamber 108 and three polymer waveguides 126, a first device 186 including the light source 104 and the three optical detectors 106 and a second device 188 including the sample chamber 108 and the three polymer waveguides 126, wherein the second device 188 may be detachably coupled with the first device 186 via a socket coupling 194 according to an embodiment.

FIG. 14 may be similar to FIG. 7, FIG. 8 and FIG. 9 except for the socket coupling 194 between the first device 186 and the second device 188. FIG. 14 shows the socket coupling 194 between the first device 186 and the second device 188 while none of FIG. 7, FIG. 8 or FIG. 9 shows any coupling.

The socket coupling 194 may include a socket (not shown) positioned on the first device 186 and a protrusion (not shown) positioned on the second device 188. The protrusion on the second device 188 may be configured so as to allow the second device 188 to be detachably coupled with the first device 186. The direction of the insertion of the second device 188 into the first device 186 may be as shown by the arrows.

Figure 15:
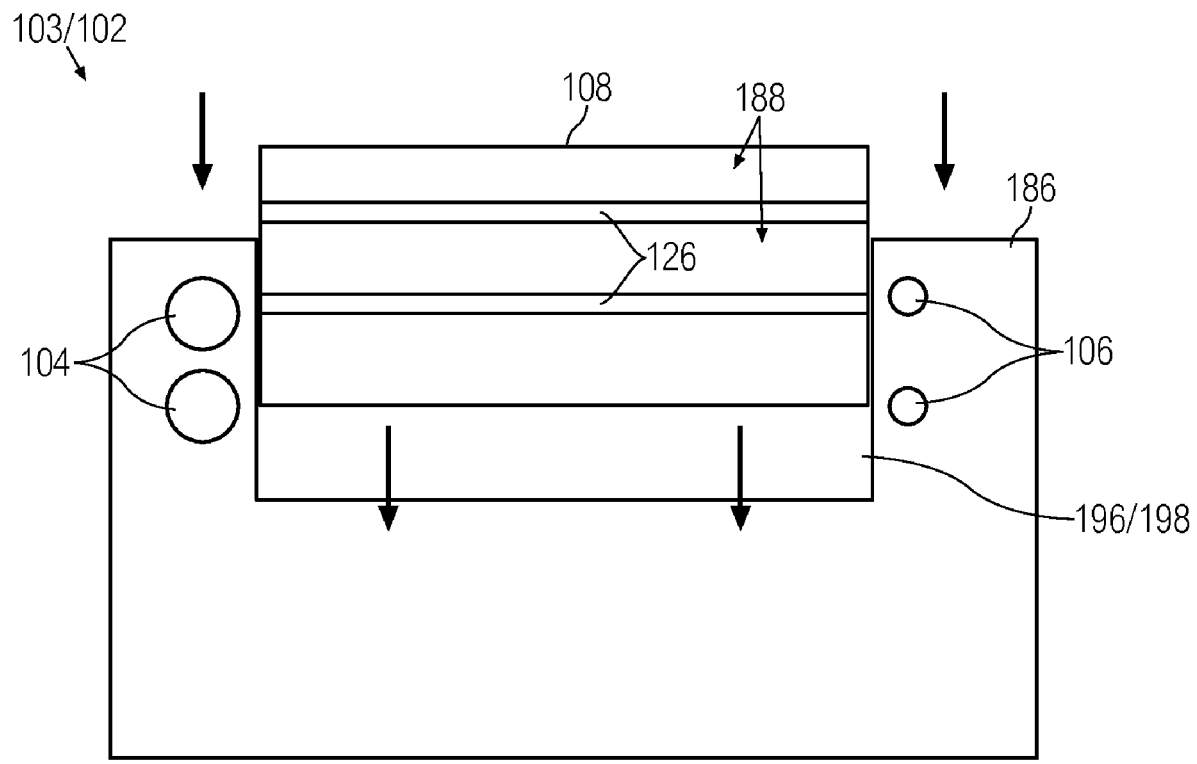
FIG. 15 shows a top view of a sensor arrangement including a sensor element with two light sources, two optical detectors, a sample chamber and two polymer waveguides, a first device including the two light sources and the two optical detectors and a second device including the sample chamber and the two polymer waveguides, wherein the second device is detachably coupled with the first device via a slot coupling according to an embodiment.

FIG. 15 shows a top view of a sensor arrangement 103 including a sensor element 102 with two light sources 104, two optical detectors 106, a sample chamber 108 and two polymer waveguides 126, a first device 186 including the two light sources 104 and the two optical detectors 106 and a second device 188 including the sample chamber 108 and the two polymer waveguides 126, wherein the second device 188 may be detachably coupled with the first device 186 via a slot coupling 196 according to an embodiment.

FIG. 15 shows a modification of the coupling between the first device 186 and the second device 188 from FIG. 14.

The slot coupling 196 may include a slot 198 positioned on the first device 186 and the second device 188 may be configured so as to allow the second device 188 to be positioned or slot into the slot 198 of the first device 186. This slot coupling 196 may allow the second device 188 to be detachably coupled with the first device 186. The direction of the insertion of the second device 188 into the first device 186 may be as shown by the arrows.

Figure 16:
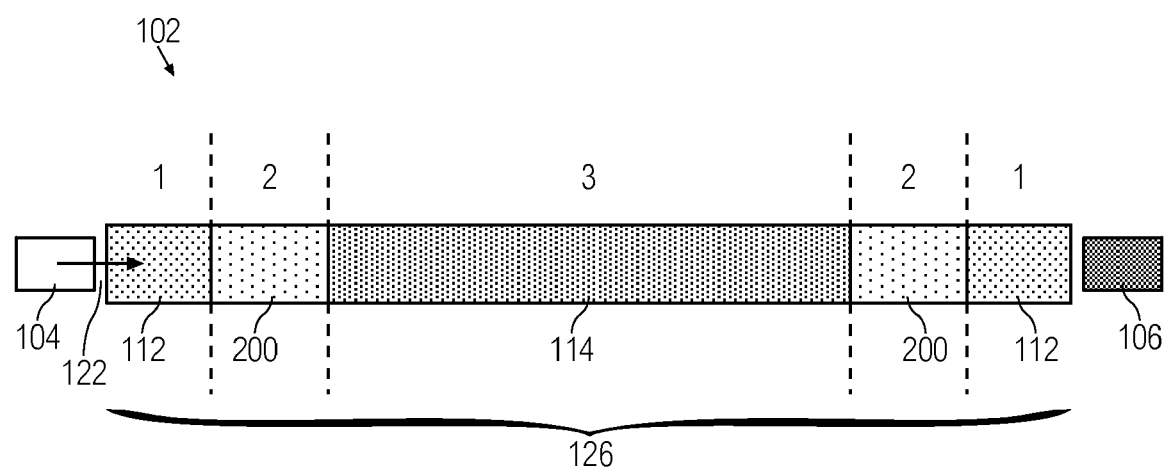
FIG. 16 shows a sensor element with a light source, an optical detector and a polymer waveguide including a first contact portion, a second contact portion and an intermediate contact portion positioned between the first contact portion and the second contact portion according to an embodiment.

FIG. 16 shows a sensor element 102 with a light source 104, an optical detector 106 and a polymer waveguide 126 including a first contact portion 112, a second contact portion 114 and an intermediate contact portion 200 positioned between the first contact portion 112 and the second contact portion 114 according to an embodiment.

The polymer waveguide 126 may allow the coupling of the input light 122 from the light source 104 to the optical detector 106. The first contact portion 112, the intermediate contact portion 200 and the second contact portion 114 may be of the same or different structure from each other. Further, the first contact portion 112, the intermediate contact portion 200 and the second contact portion 114 may be of the same or different material from each other.

Figure 17A:
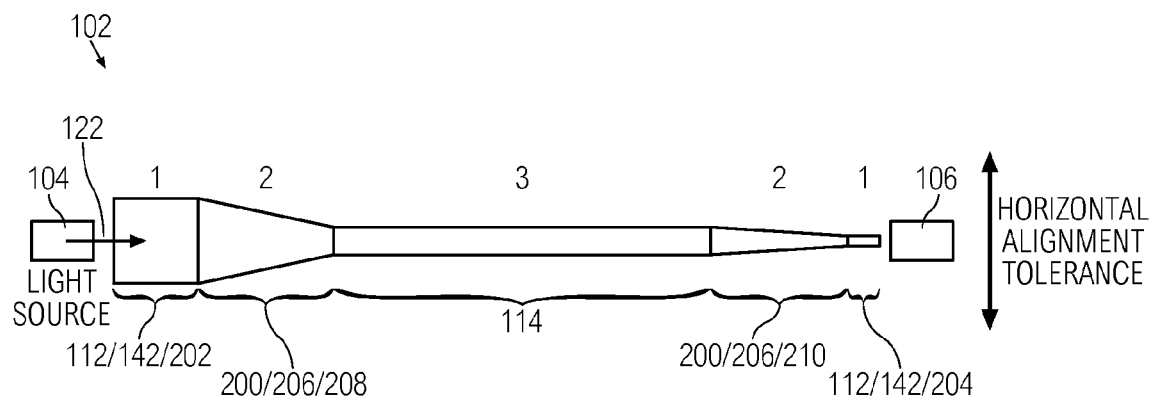
FIG. 17A and FIG. 17B respectively show a top view and a side view of a sensor element with a light source, an optical detector and a polymer waveguide including a first contact portion, a second contact portion and an intermediate contact portion positioned between the first contact portion and the second contact portion according to an embodiment.
Figure 17B:
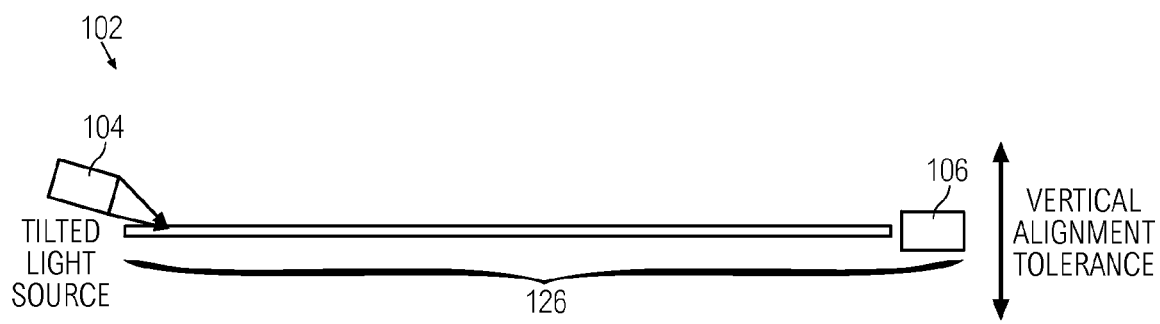

FIG. 17A and FIG. 17B respectively show a top view and a side view of a sensor element 102 with a light source 104, an optical detector 106 and a polymer waveguide 126 including a first contact portion 112, a second contact portion 114 and an intermediate contact portion 200 positioned between the first contact portion 112 and the second contact portion 114 according to an embodiment.

From FIG. 17A, the first contact portion 112 may include two first partial contact portions 142, for example a portion 202 optically coupling the light source 104 to the second contact portion 114 and a portion 204 optically coupling the second contact portion 114 to the optical detector 106. The intermediate contact portion 200 may also include two intermediate partial contact portions 206, for example a portion 208 optically coupling the portion 202 to the second contact portion 114 and a portion 210 optically coupling the second contact portion 114 to the portion 204.

In order to minimise horizontal misalignment amongst the light source 104, the polymer waveguide 126 and the optical detector 106, the respective dimensions of the first contact portion 112, the intermediate contact portion 200 and the second contact portion 114 may be as shown in FIG. 17A. In relation to the first contact portion 112, the dimension of the portion 202 optically coupling the light source 104 to the portion 208 may be larger than the portion 204 optically coupling the portion 210 to the optical detector 106. As an example, the dimensions of the portion 202 optically coupling the light source 104 to the portion 208 may be larger than the light spot size of the input light 122 from the light source 104 if the polymer waveguide 126 may be used to couple the input light 122 from the light source 104 to the polymer waveguide 126. The dimensions of the portion 204 optically coupling the portion 210 to the optical detector 106 may be smaller than the active area of the optical detector 106. Further, the intermediate contact portion 200 may be tapered in shape. As an example, the portion 208 optically coupling the portion 202 to the second contact portion 114 may be tapered in the direction from the portion 208 towards the second contact portion 114 and the portion 210 optically coupling the second contact portion 114 to the portion 204 may be tapered in the direction from the second contact portion 114 towards the portion 204. The respective portion 208 optically coupling the portion 202 to the second contact portion 114 and the portion 210 optically coupling the second contact portion 114 to the portion 204 may be shaped as such so as to allow a smooth transition for the input light 122 travelling from the light source 104 towards the optical detector 106 and thereby light loss may be minimised. In addition, the second contact portion 114 may include any of the structures as mentioned in FIG. 1 to FIG. 6.

The difference in dimension between the portion 202 optically coupling the light source 104 to the portion 208 and the light spot size of the input light 122 from the light source 104 may be about 2 mm. The difference in dimension between the portion 204 optically coupling the portion 210 to the optical detector 106 and the active area of the optical detector 106 may be about 2 mm.

In order to minimise vertical misalignment amongst the light source 104, the polymer waveguide 126 and the optical detector 106, the light source 104 may be tilted relative to a horizontal plane of the polymer waveguide 126 as shown in FIG. 17B. The light source 104 may be tilted at any suitable angle relative to the horizontal plane of the polymer waveguide 126. Tilting the light source 104 may minimise the effect of a possible vertical misalignment. However, if a mechanical alignment of the respective components within the sensor element 102 may be accurate, there may not be a need to tilt the light source 104 relative to the horizontal plane of the polymer waveguide 126. Further, if the thickness of the polymer waveguide 126 may be substantial, it may also be sufficient to accommodate a certain tolerance of the vertical misalignment. Therefore, it may also not be necessary to tilt the light source 104 relative to the horizontal plane of the polymer waveguide 126.

Figure 18:
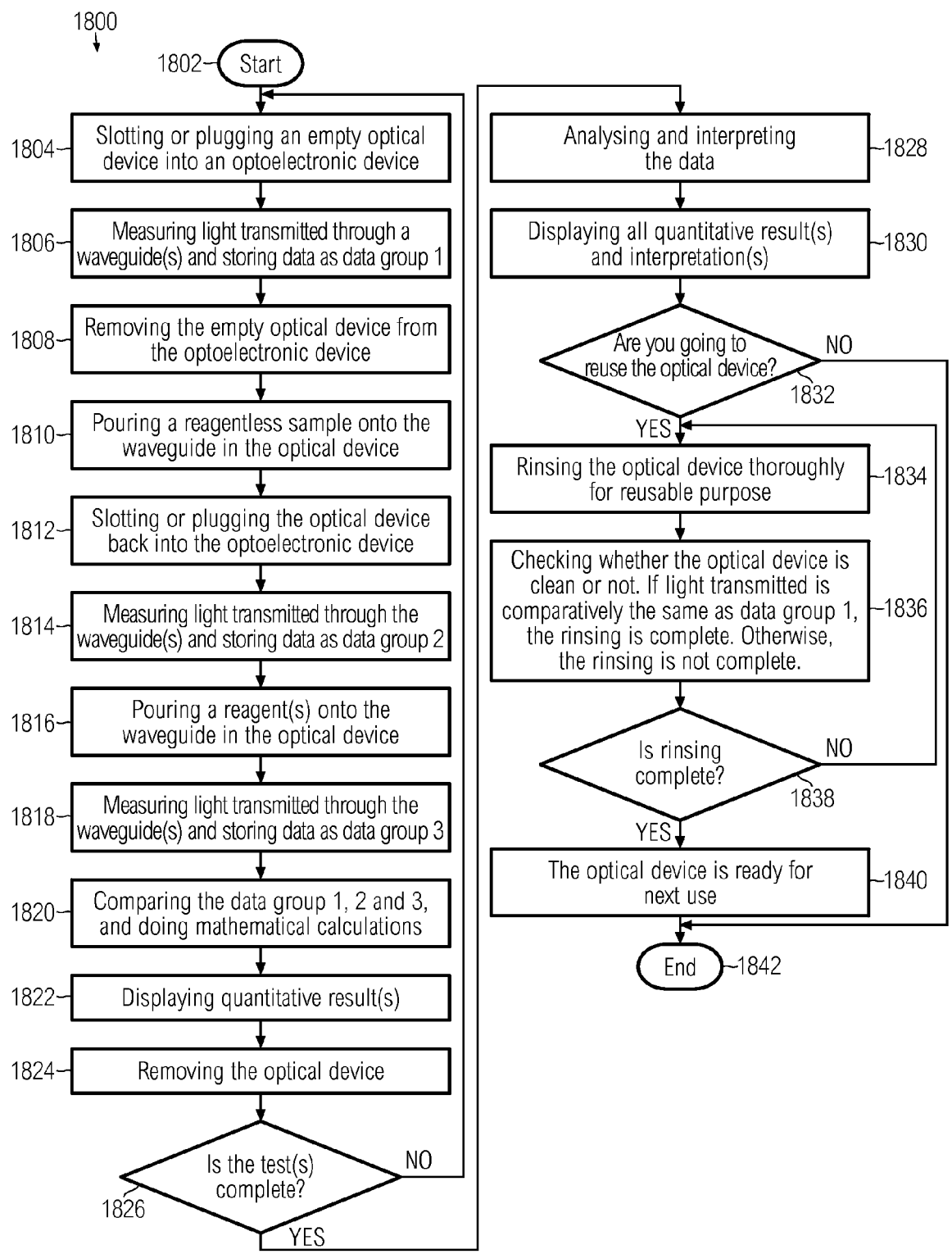
FIG. 18 shows a flow diagram of a method of using a sensor element, the sensor element with at least one polymer waveguide for sensing an analyte of interest according to an embodiment.

FIG. 18 shows a flow diagram of a method 1800 of using a sensor element 102, the sensor element 102 with at least one polymer waveguide 126 for sensing an analyte of interest according to an embodiment.

An example of the sensor element 102 may be as shown in FIG. 13 including an additional coupling between the first device 186 and the second device 188 such that the second device 188 may be detachably coupled with the first device 186. The first device 186 may be termed an optoelectronic device and the second device 188 may be termed an optical device.

The method 1800 begins at 1802. In 1804, an empty optical device 188 may be slotted or plugged into an optoelectronic device 186. Then in 1806, light transmitted through a polymer waveguide(s) 126 may be measured and the data may be stored as data group 1. In 1808, the empty optical device 188 may be removed from the optoelectronic device 186. Then in 1810, a reagentless sample may be poured onto the polymer waveguide (s) 126 in the optical device 188. In 1812, the optical device 188 may be slotted or plugged back into the optoelectronic device 186. In 1814, the light transmitted through the polymer waveguide(s) 126 may be measured and the data may be stored as data group 2. In 1816, a reagent may be poured onto the polymer waveguide 126 in the optical device 188. In 1818, the light transmitted through the polymer waveguide(s) 126 may be measured and the data may be stored as data group 3. In 1820, the data groups 1, 2 and 3 may be compared and mathematical calculations may be performed. In 1822, the quantitative result(s) may be displayed. In 1824, the optical device 188 may be removed from the optoelectronic device 186. In 1826, a check may be performed to assess if the test(s) may be complete. If no, the method 1800 may proceed to the beginning of the method 1800 in 1802. If yes, the method 1800 may proceed to 1828 where the data may be analysed and interpreted. Then in 1830, all quantitative result(s) and interpretation may be displayed. In 1832, a check may be performed to assess if a user may be reusing the optical device 188. If no, the method 1800 may proceed to the end of the method 1800 at 1842. If yes, the method 1800 may proceed to 1834 where the optical device 188 may be rinsed thoroughly for reusable purpose. Then in 1836, the optical device 188 may be checked to assess if the optical device 188 may be clean or not. If light transmitted may be comparatively the same as the data group 1, the rinsing may be completed. Otherwise, the rinsing may not be complete. In 1838, a check may be performed to assess if the rinsing may be complete. If no, the method 1800 may proceed to 1834 where the optical device 188 may be rinsed thoroughly for reusable purpose. If yes, the method 1800 may proceed to 1840 where the optical device 188 may be ready for next use. The method 1800 may end at 1842.

Figure 19:
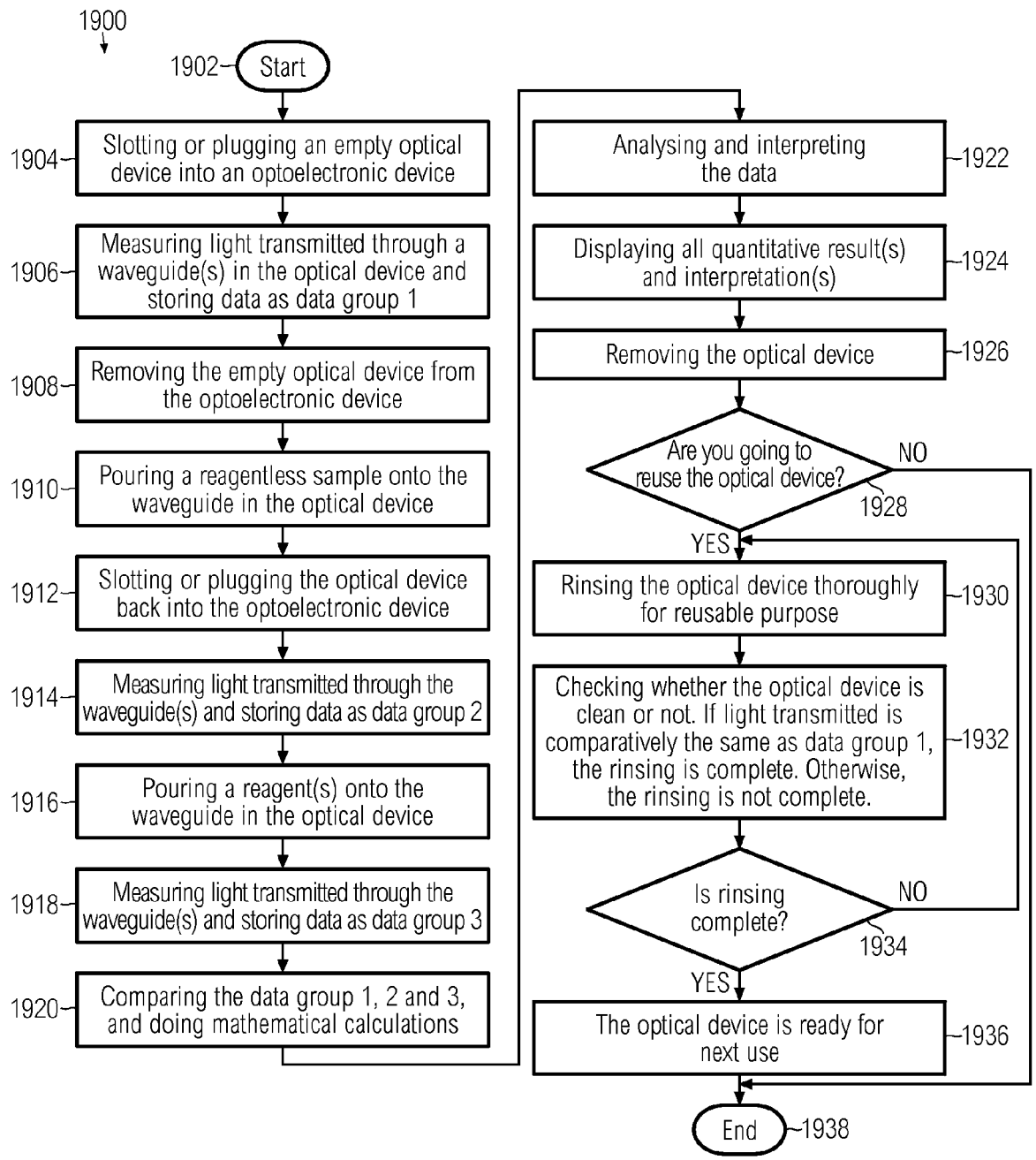
FIG. 19 shows a flow diagram of a method of using a sensor element, the sensor element with a plurality of polymer waveguides, each polymer waveguide for sensing one of the plurality of analytes of interest according to an embodiment.

FIG. 19 shows a flow diagram of a method 1900 of using a sensor element 102, the sensor element 102 with a plurality of polymer waveguides 126, each polymer waveguide 126 for sensing one of the plurality of analytes of interest according to an embodiment.

Like in FIG. 18, an example of the sensor element 102 may be as shown in FIG. 7, FIG. 8, FIG. 9 or FIG. 10 including an additional coupling between the first device 186 and the second device 188 such that the second device 188 may be detachably coupled with the first device 186. The first device 186 may be termed an optoelectronic device and the second device 188 may be termed an optical device.

The method 1900 begins at 1902. In 1904, an empty optical device 188 may be slotted or plugged into an optoelectronic device 186. Then in 1906, light transmitted through a polymer waveguide(s) 126 may be measured and the data may be stored as data group 1. In 1908, the empty optical device 188 may be removed from the optoelectronic device 186. Then in 1910, a reagentless sample may be poured onto the polymer waveguide(s) 126 in the optical device 188. In 1912, the optical device 188 may be slotted or plugged back into the optoelectronic device 186. In 1914, the light transmitted through the polymer waveguide(s) 126 may be measured and the data may be stored as data group 2. In 1916, a reagent may be poured onto the polymer waveguide 126 in the optical device 188. In 1918, the light transmitted through the polymer waveguide(s) 126 may be measured and the data may be stored as data group 3. In 1920, the data groups 1, 2 and 3 may be compared and mathematical calculations may be performed. In 1922, the data may be analysed and interpreted. Then in 1924, all quantitative result(s) and interpretation may be displayed. In 1926, the optical device 188 may be removed from the optoelectronic device 186. In 1928, a check may be performed to assess if a user may be reusing the optical device 188. If no, the method 1900 may proceed to the end of the method 1900 at 1938. If yes, the method 1900 may proceed to 1930 where the optical device 188 may be rinsed thoroughly for reusable purpose. Then in 1932, the optical device 188 may be checked to assess if the optical device 188 may be clean or not. If light transmitted may be comparatively the same as the data group 1, the rinsing may be complete. Otherwise, the rinsing may not be complete. In 1934, a check may be performed to assess if the rinsing may be complete. If no, the method 1900 may proceed to 1930 where the optical device 188 may be rinsed thoroughly for reusable purpose. If yes, the method 1900 may proceed to 1936 where the optical device 188 may be ready for next use. The method 1900 may end at 1938.

Figure 20:
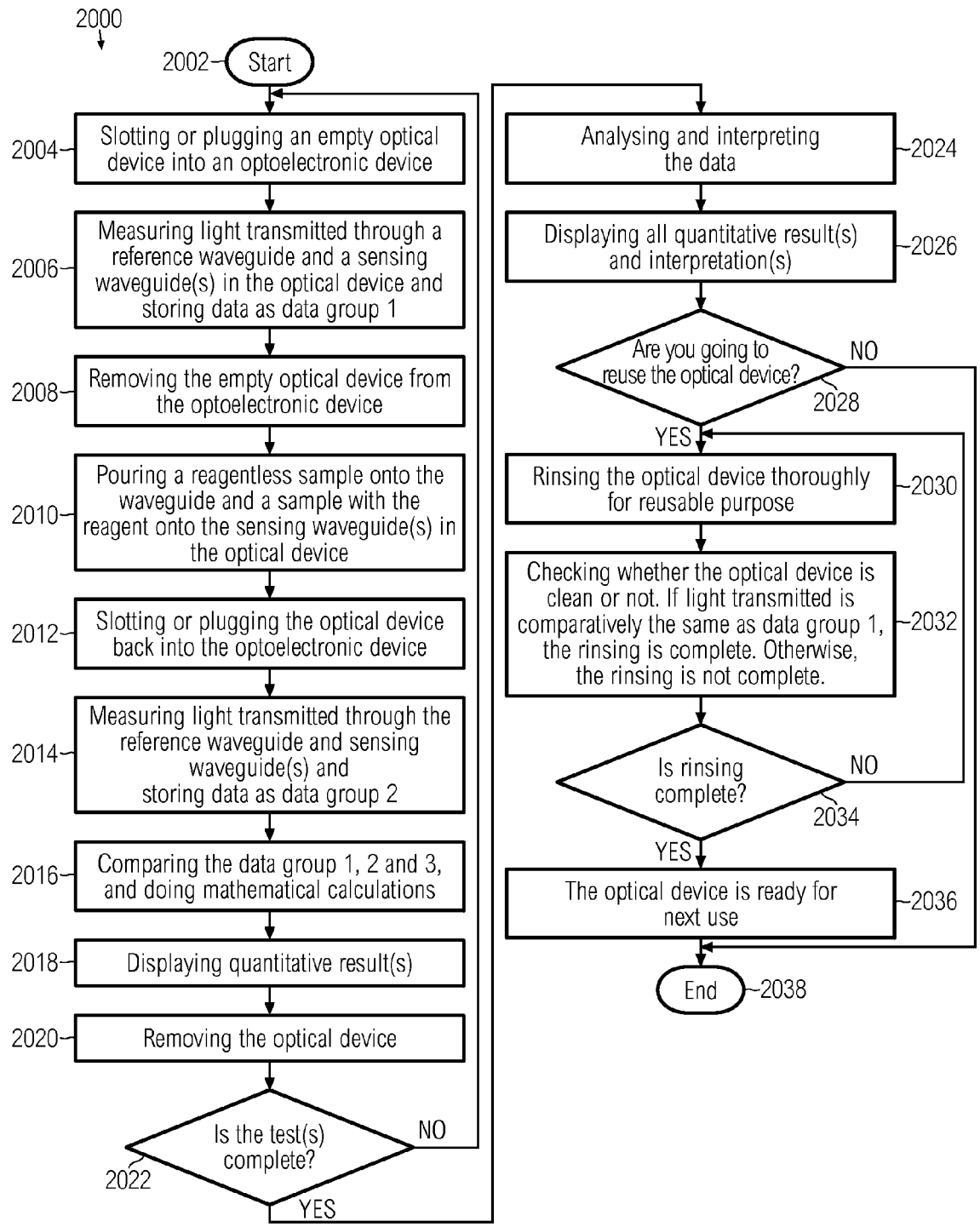
FIG. 20 shows a flow diagram of a method of using a sensor element, the sensor element with a polymer waveguide for reference and another polymer waveguide for sensing an analyte of interest according to an embodiment.

FIG. 20 shows a flow diagram of a method 2000 of using a sensor element 102, the sensor element 102 with a polymer waveguide 212 for reference and another polymer waveguide 214 for sensing an analyte of interest according to an embodiment.

An example of the sensor element 102 may be as shown in either of FIG. 7, FIG. 8, or FIG. 9 with only two polymer waveguides 126 instead of three polymer waveguides and including an additional coupling between the first device 186 and the second device 188 such that the second device 188 may be detachably coupled from the first device 186. Another example of the sensor element 102 may be as shown in FIG. 10 where a polymer waveguide 126 is housed in a sample chamber 108 and a further polymer waveguide 180 may be housed in a further sample chamber 176. The sensor element 102 may also include an additional coupling between the first device 186 and the second device 188 such that the second device 188 may be detachably coupled from the first device 186.

One of the two polymer waveguides 126 may be used for reference and termed the reference waveguide 212 and the other polymer waveguide 126 may be used for sensing the analyte of interest and termed the sensing waveguide 214. The first device 186 may be termed an optoelectronic device and the second device 188 may be termed an optical device.

The method 2000 begins at 2002. In 2004, an empty optical device 188 may be slotted or plugged into an optoelectronic device 186. Then in 2006, light transmitted through a reference waveguide 212 and a sensing waveguide(s) 214 in the optical device 188 may be respectively measured and the data may be stored as data group 1. In 2008, the empty optical device 188 may be removed from the optoelectronic device 186. Then in 2010, a reagentless sample may be poured onto the reference waveguide 212 and a sample(s) with reagent may be poured onto the sensing waveguide(s) 214 in the optical device 188. In 2012, the optical device 188 may be slotted or plugged back into the optoelectronic device 186. In 2014, the light transmitted through the reference waveguide 212 and the sensing waveguide(s) 214 may be respectively measured and the data may be stored as data group 2. In 2016, the data group 2 may be compared with the data group 1 and mathematical calculations may be performed. In 2018, the quantitative result(s) may be displayed. In 2020, the optical device 188 may be removed from the optoelectronic device 186. In 2022, a check may be performed to assess if the test(s) may be complete. If no, the method 2000 may proceed to the beginning of the method 2000 in 2002. If yes, the method 2000 may proceed to 2024 where the data may be analysed and interpreted. Then in 2026, all quantitative result(s) and interpretation may be displayed. In 2028, a check may be performed to assess if a user may be reusing the optical device 188. If no, the method 2000 may proceed to the end of the method 2000 at 2038. If yes, the method 2000 may proceed to 2030 where the optical device 188 may be rinsed thoroughly for reusable purpose. Then in 2032, the optical device 188 may be checked to assess if the optical device 188 may be clean or not If light transmitted may be comparatively the same as the data group 1, the rinsing may be completed. Otherwise, the rinsing may not be complete. In 2034, a check may be performed to assess if the rinsing may be complete. If no, the method 2000 may proceed to 2030 where the optical device 188 may be rinsed thoroughly for reusable purpose. If yes, the method 2000 may proceed to 2036 where the optical device 188 may be ready for next use. The method 2000 may end at 2038.

Figure 21:
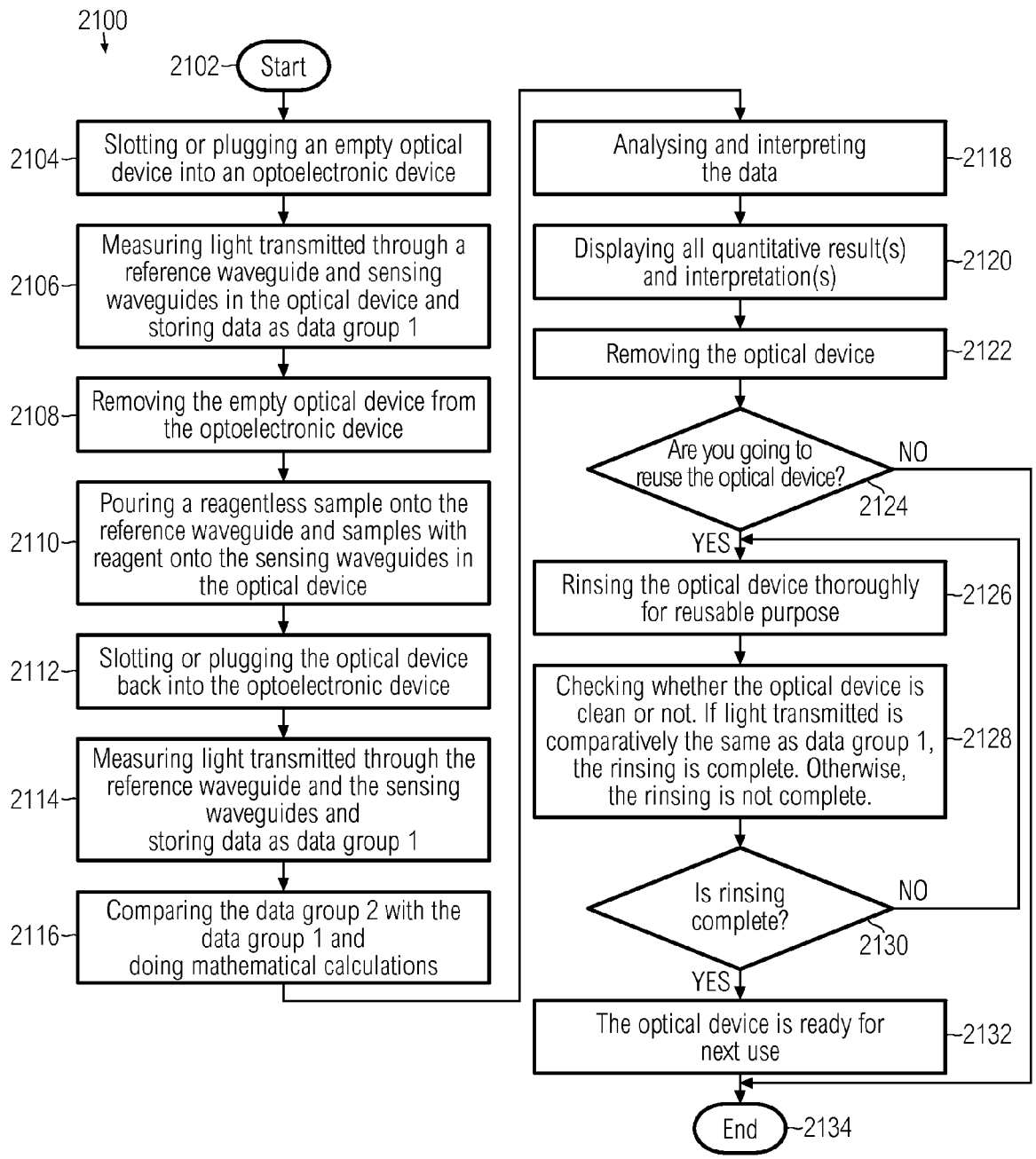
FIG. 21 shows a flow diagram of a method of using a sensor element, the sensor element with a polymer waveguide for reference and a plurality of polymer waveguides, each polymer waveguide for sensing one of the plurality of analytes of interest according to an embodiment.

FIG. 21 shows a flow diagram of a method 2100 of using a sensor element 102, the sensor element 102 with a polymer waveguide 212 for reference and a plurality of polymer waveguides 214, each polymer waveguide 214 for sensing one of the plurality of analytes of interest according to an embodiment.

Like in FIG. 20, an example of the sensor element 102 may be as shown in either of FIG. 7, FIG. 8 or FIG. 9 with three or more polymer waveguides and including an additional coupling between the first device 186 and the second device 188 such that the second device 188 may be detachably coupled with the first device 186. Another example of the sensor element 102 may be as shown in FIG. 10 with additional polymer waveguides 126 or further polymer waveguides 180 and sample chambers 108 or further sample chambers 176. The sensor element 102 may also include an additional coupling between the first device 186 and the second device 188 such that the second device 188 may be detachably coupled with the first device 186.

One of the plurality of polymer waveguides 126 may be used for reference and termed the reference waveguide 212 and the rest of the polymer waveguides 126 may be used for sensing the analyte of interest and termed the sensing waveguides 214. The first device 186 may be termed an optoelectronic device and the second device 188 may be termed an optical device.

The method 2100 begins at 2102. In 2104, an empty optical device 188 may be slotted or plugged into an optoelectronic device 186. Then in 2106, light transmitted through a reference waveguide 212 and sensing waveguides 214 in the optical device 188 may be respectively measured and the data may be stored as data group 1. In 2108, the empty optical device 188 may be removed from the optoelectronic device 186. Then in 2110, a reagentless sample may be poured onto the reference waveguide 212 and samples with reagent may be poured onto the sensing waveguides 214 in the optical device 188. In 2112, the optical device 188 may be slotted or plugged back into the optoelectronic device 186. In 2114, the light transmitted through the reference waveguide 212 and the sensing waveguides 214 may be respectively measured and the data may be stored as data group 2. In 2116, the data group 2 may be compared with the data group 1 and mathematical calculations may be performed. In 2118, the data may be analysed and interpreted. Then in 2120, all quantitative result (s) and interpretation may be displayed. In 2122, the optical device 188 may be removed from the optoelectronic device 186. In 2124, a check may be performed to assess if a user may be reusing the optical device 188. If no, the method 2100 may proceed to the end of the method 2100 at 2134. If yes, the method 2100 may proceed to 2126 where the optical device 188 may be rinsed thoroughly for reusable purpose. Then in 2128, the optical device 188 may be checked to assess if the optical device 188 may be clean or not. If light transmitted may be comparatively the same as the data group 1, the rinsing may be completed. Otherwise, the rinsing may not be complete. In 2130, a check may be performed to assess if the rinsing may be completed. If no, the method 2100 may proceed to 2126 where the optical device 188 may be rinsed thoroughly for reusable purpose. If yes, the method 2100 may proceed to 2132 where the optical device 188 may be ready for next use. The method 2100 may end at 2134.

Figure 22:
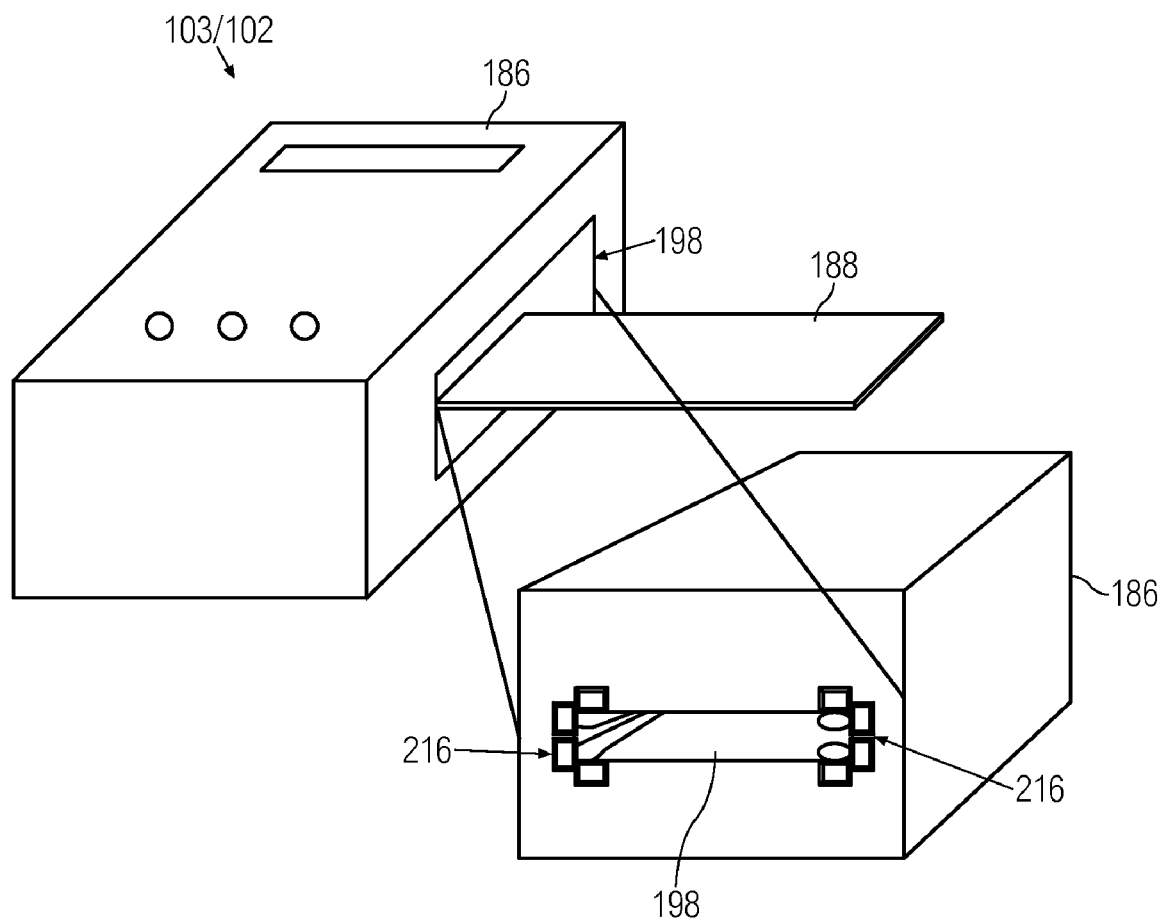
FIG. 22 shows a perspective view of a sensor arrangement including a sensor element, a first device, a second device and a guiding element, the guiding element configured to allow the second device to be guided into the first device according to an embodiment.

FIG. 22 shows a perspective view of a sensor arrangement 103 including a sensor element 102, a first device 186, a second device 188 and a guiding element 216, the guiding element 216 configured to allow the second device 188 to be guided into the first device 186 according to an embodiment.

The first device 186 may include a slot or socket 198 configured to allow an insertion of the second device 188. The guiding element or mechanical aligner 216 may be positioned at four corners of the slot or socket 198 so as to allow the second device 188 to be mechanically guided into the first device 186. The guiding element 216 may include soft and elastic hemi-cylindrical rubbers and elastic springs. The position of the guiding element 216 may help with self alignment amongst the light source (not shown) and the optical detector (not shown) housed within the first device 186 and the polymer waveguide (not shown) housed within the second device 188.

Every time when a user pushes the second device 188, which may include at least one polymer waveguide sensors into the slot or socket 198, the second device 188 may be tightly guided by the guiding element 216 at a particular position within the first device 186, which may enhance the light coupling efficiency from the light source to the polymer waveguide and from the polymer waveguide to the optical detector.

Figure 23:
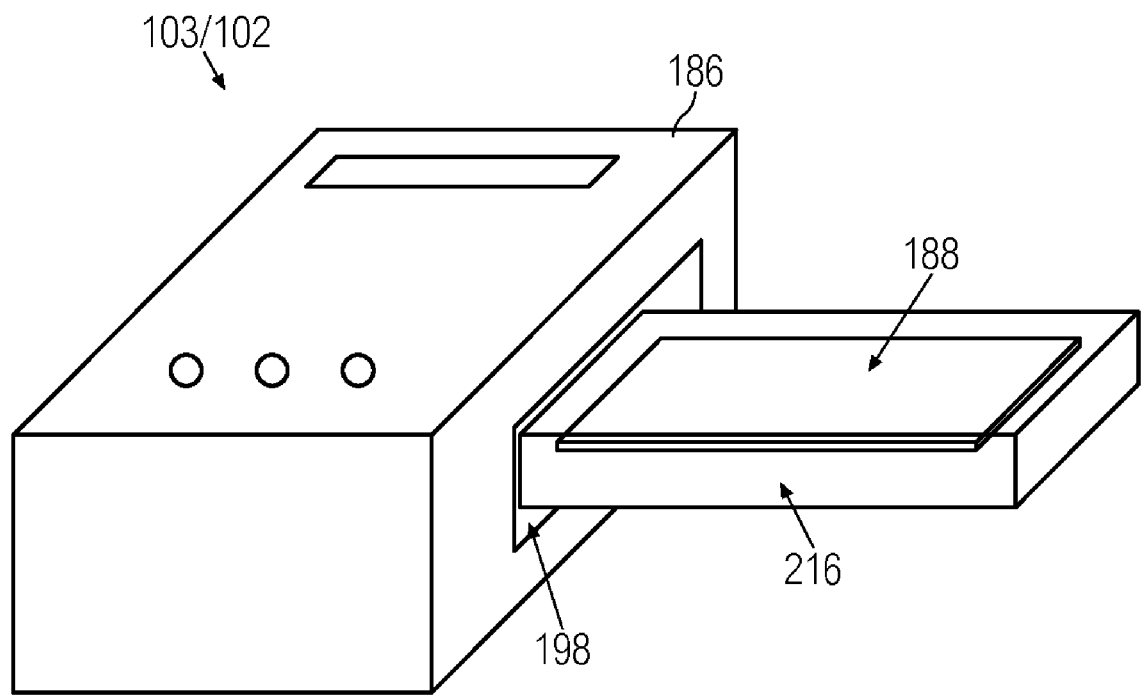
FIG. 23 shows a perspective view of a sensor arrangement including a sensor element, a first device, a second device and a guiding element, the guiding element configured to allow the second device to be guided into the first device according to an embodiment.

FIG. 23 shows a perspective view of a sensor arrangement 103 including a sensor element 102, a first device 186, a second device 188 and a guiding element 216, the guiding element 216 configured to allow the second device 188 to be guided into the first device 186 according to an embodiment.

The guiding element 216 may include an optical device grabber which may be configured so as to accommodate or slot the second device 188. The first device 186 may include a slot or socket 198 configured to allow an insertion of the guiding element 216. When in use, a user may place the second device 188 onto the guiding element 216 and the guiding element 216 may load the second device 188 into the first device 186. The guiding element 216 may be equipped with a closed loop automatic positional system that may be able to optimise the light coupling from the light source (not shown) to the polymer waveguide (not shown) and from the polymer waveguide to the optical detector (not shown). The sensor element 102 including the guiding element 216 may improve the alignment between the light source (not shown) and the optical detector (not shown) housed within the first device 186 and the polymer waveguide (not shown) housed within the second device 188 and thereby minimise the effect of human errors and carelessness.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A sensor element comprising:
a light input configured to receive input light,
a sample chamber configured to accommodate a sample; and
at least one polymer waveguide optically coupling the light input with the sample chamber, the at least one polymer waveguide comprising a first contact portion and a second contact portion, wherein at least a portion of the second contact portion is arranged in the sample chamber;
wherein the second contact portion has a different structure than the first contact portion so that a change of the light intensity of the input light passing through the second contact portion may be caused due to an interaction between the input light passing through the second contact portion and the sample, wherein the change of the light intensity of the input light passing through the second contact portion is different from the change of the light intensity of the input light passing through the first contact portion;
wherein the second contact portion is configured so as to allow an increased interaction between the input light and the sample as compared to the first contact portion; and
wherein the second contact portion comprises at least two shaped portions positioned along a common axis, each shaped portion separated by a gap.

2. The sensor element of claim 1, further comprising:
at least one optical detector positioned in optical communication with the at least one polymer waveguide for detecting a resultant light after the input light travels along the at least one polymer waveguide and through the sample chamber.

3. The sensor element of claim 2,
wherein the at least one optical detector comprises one or more of a group consisting of a photodiode, a photomultiplier, a charged-coupled device detector, a light dependent resistor, a phototransistor and a photocell.

4. The sensor element of claim 2, further comprising:
at least one filter configured to output a pre-determined wavelength of the resultant light, the at least one filter being positioned in the optical path between the at least one polymer waveguide and the at least one optical detector.

5. The sensor element of claim 4,
wherein the at least one filter comprises one or more of a group consisting of a Bragg grating filter, a Fabry-Perot filter, an absorptive filter, a dichroic filter and an interference filter.

6. The sensor element of claim 1,
wherein the first contact portion comprises a continuous portion with a constant diameter.

7. The sensor element of claim 1,
wherein the second contact portion comprises a spiral portion or a U-shaped portion.

8. The sensor element of claim 1, further comprising:
a light source configured to provide the input light to the light input.

9. The sensor element of claim 8,
wherein the light source comprises one or more of a group consisting of a laser, a white light, a fluorescent light, a laser diode, a light emitting diode, an organic light emitting diode, a gas discharge light source, an incandescent lamp and an electroluminescent lamp.

10. The sensor element of claim 1, further comprising:
a further sample chamber configured to accommodate a further sample.

11. The sensor element of claim 10, further comprising:
a further polymer waveguide optically coupling the further sample chamber with the light input.

12. The sensor element of claim 11, further comprising:
a further optical detector, the further optical detector positioned in optical communication with the further polymer waveguide for detecting a further resultant light after the input light travels along the further polymer waveguide and through the further sample chamber.

13. The sensor element of claim 1,
wherein the sample comprises macromolecular biomolecules.

14. The sensor element of claim 1,
wherein the at least one polymer waveguide further comprises an intermediate contact portion, the intermediate contact portion positioned between the first contact portion and the second contact portion.

15. A sensor arrangement, comprising:
a sensor element comprising
a light input configured to receive input light,
a sample chamber configured to accommodate a sample;
at least one polymer waveguide optically coupling the light input with the sample chamber, the at least one polymer waveguide comprising a first contact portion and a second contact portion, wherein at least a portion of the second contact portion is arranged in the sample chamber;
at least one optical detector positioned in optical communication with the at least one polymer waveguide for detecting a resultant light after the input light travels along the at least one polymer waveguide and through the sample chamber;

a light source configured to provide the input light to the light input;

a first device comprising the light source and the at least one optical detector; and a second device comprising the sample chamber and the at least one polymer waveguide;

wherein the second contact portion has a different structure than the first contact portion so that a change of the light intensity of the input light passing through the second contact portion may be caused due to an interaction between the input light passing through the second contact portion and the sample, wherein the change of the light intensity of the input light passing through the second contact portion is different from the change of the light intensity of the input light passing through the first contact portion;

wherein the second contact portion is configured so as to allow an increased interaction between the input light and the sample as compared to the first contact portion; and wherein the second contact portion comprises at least two shaped portions positioned along a common axis, each shaped portion separated by a gap.

16. The sensor arrangement of claim 15, wherein the second device is detachably coupled with the first device.

17. The sensor arrangement of claim 15, wherein the first device further comprises a slot or socket configured for receiving a portion of the second device.

18. The sensor arrangement of claim 15, further comprising a guiding element configured to allow the second device to be mechanically aligned to the first device.

* * * * *